United States Patent [19]
Lambert et al.

[11] Patent Number: 6,054,139
[45] Date of Patent: Apr. 25, 2000

[54] CLEANING AND/OR DISINFECTING COMPOSITION

[75] Inventors: Ronald Joseph Lambert; Moira Diane Johnston, both of Sharnbrook, United Kingdom; Eduard C. van Baggem; Gijsbertus de Goederen, both of Maarssen, Netherlands

[73] Assignee: Diversey Lever Inc., Plymouth, Mich.

[21] Appl. No.: 08/854,277

[22] Filed: May 9, 1997

[30] Foreign Application Priority Data

May 10, 1996 [EP] European Pat. Off. ............. 96201289

[51] Int. Cl.[7] .................................................. A01N 25/02
[52] U.S. Cl. ......................... 424/405; 424/406; 514/159; 514/556; 514/557; 514/559; 514/567; 514/576; 514/578
[58] Field of Search ...................... 424/405, 406; 514/159, 558, 557, 559, 567, 576, 578

[56] References Cited

U.S. PATENT DOCUMENTS

| | | | |
|---|---|---|---|
| 3,686,405 | 8/1972 | Hofmann et al. | 424/263 |
| 5,496,538 | 3/1996 | Zimmerman et al. | 424/45 |
| 5,653,970 | 8/1997 | Vermeer | 424/70.24 |

FOREIGN PATENT DOCUMENTS

| | | |
|---|---|---|
| 2165945 | of 0000 | Canada . |
| 333 143 | of 0000 | European Pat. Off. . |
| 620 013 | of 0000 | European Pat. Off. . |
| 91/10514 | of 0000 | WIPO . |

OTHER PUBLICATIONS

PTO Search print out of dipropylamine, Sep. 1998.

*Primary Examiner*—Neil S. Levy

[57] ABSTRACT

The invention relates to a cleaning and/or disinfecting composition comprising a tertiary alkyl amine and an alkyl betaine.

9 Claims, 26 Drawing Sheets

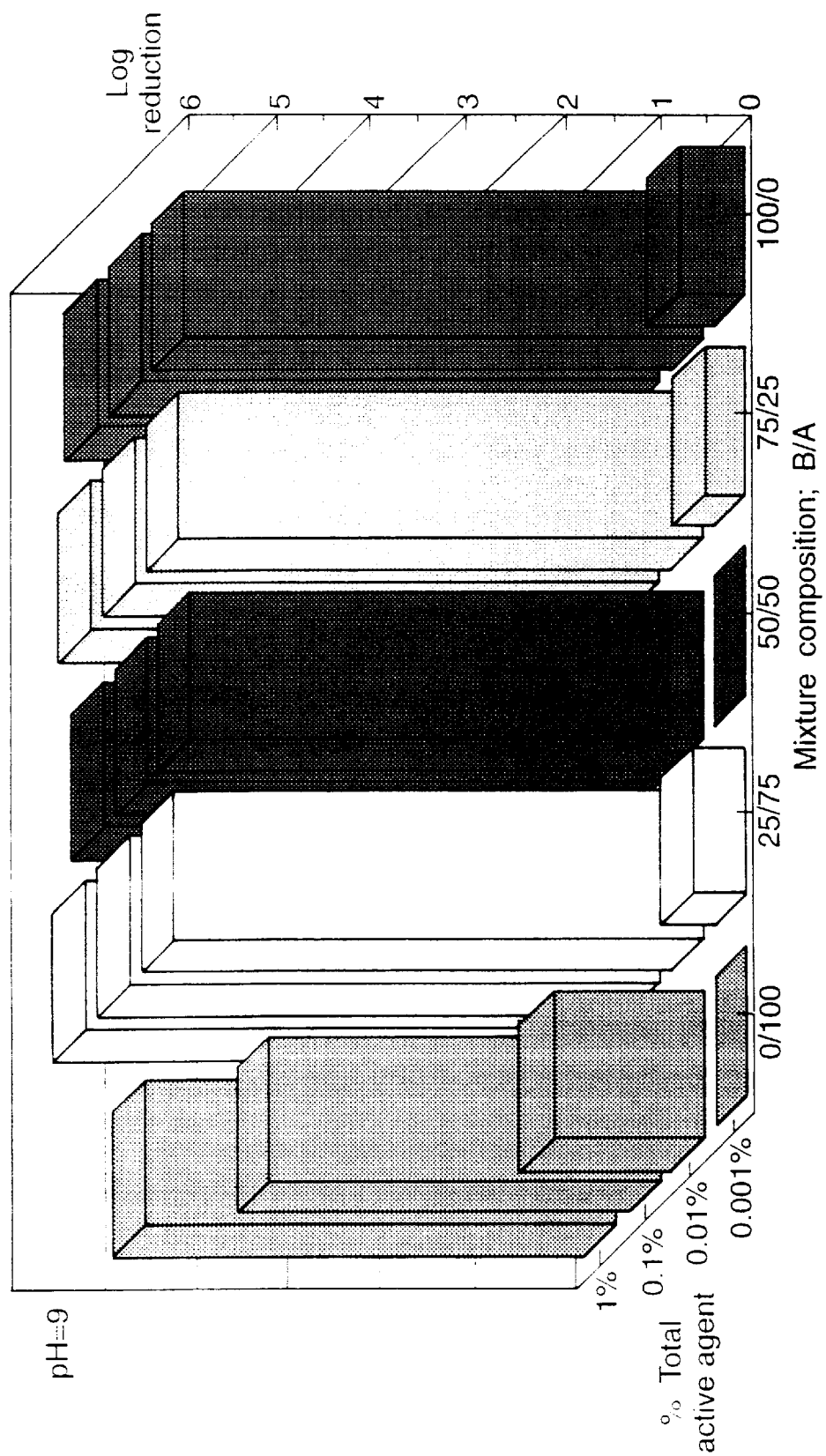

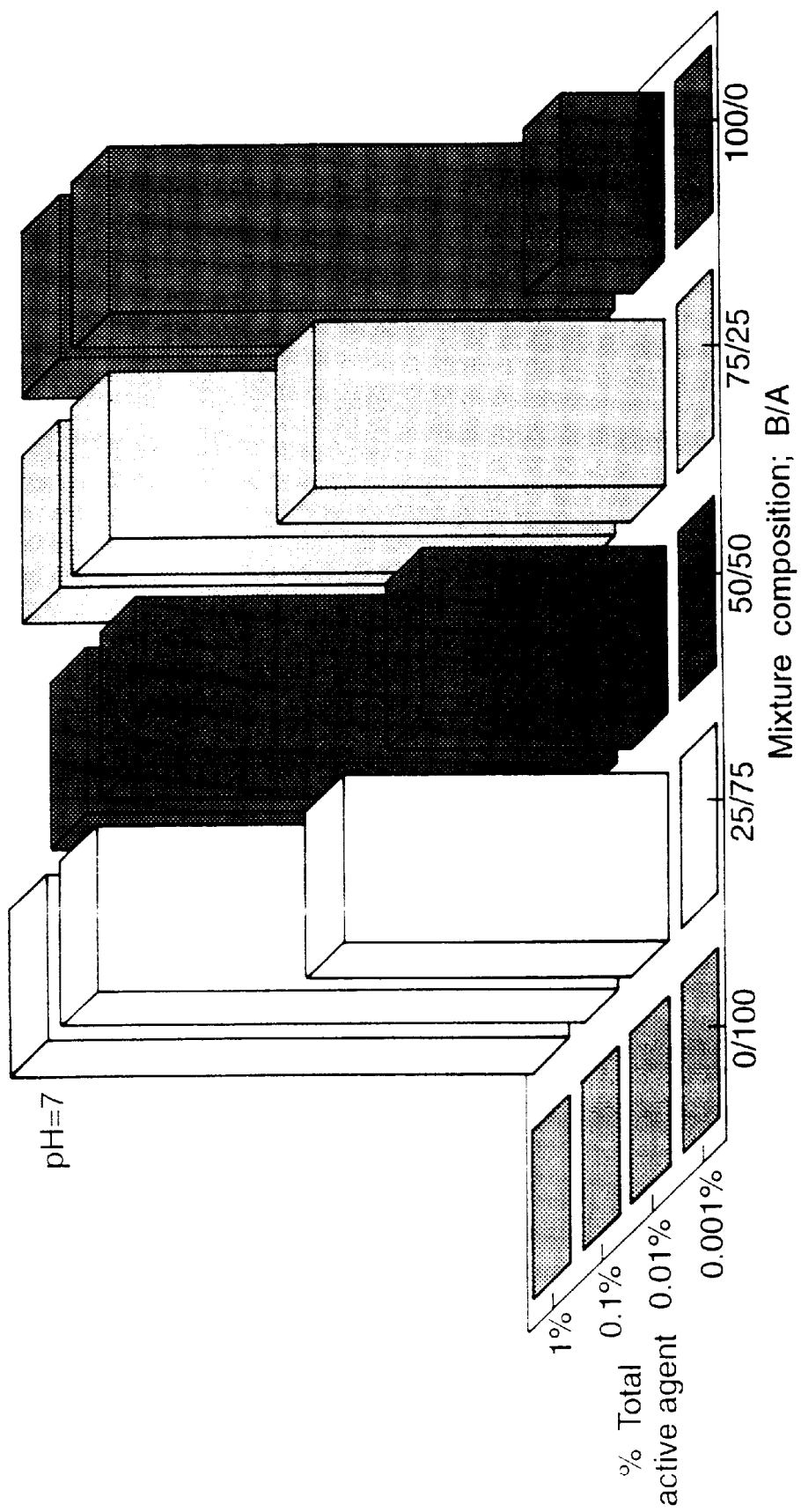

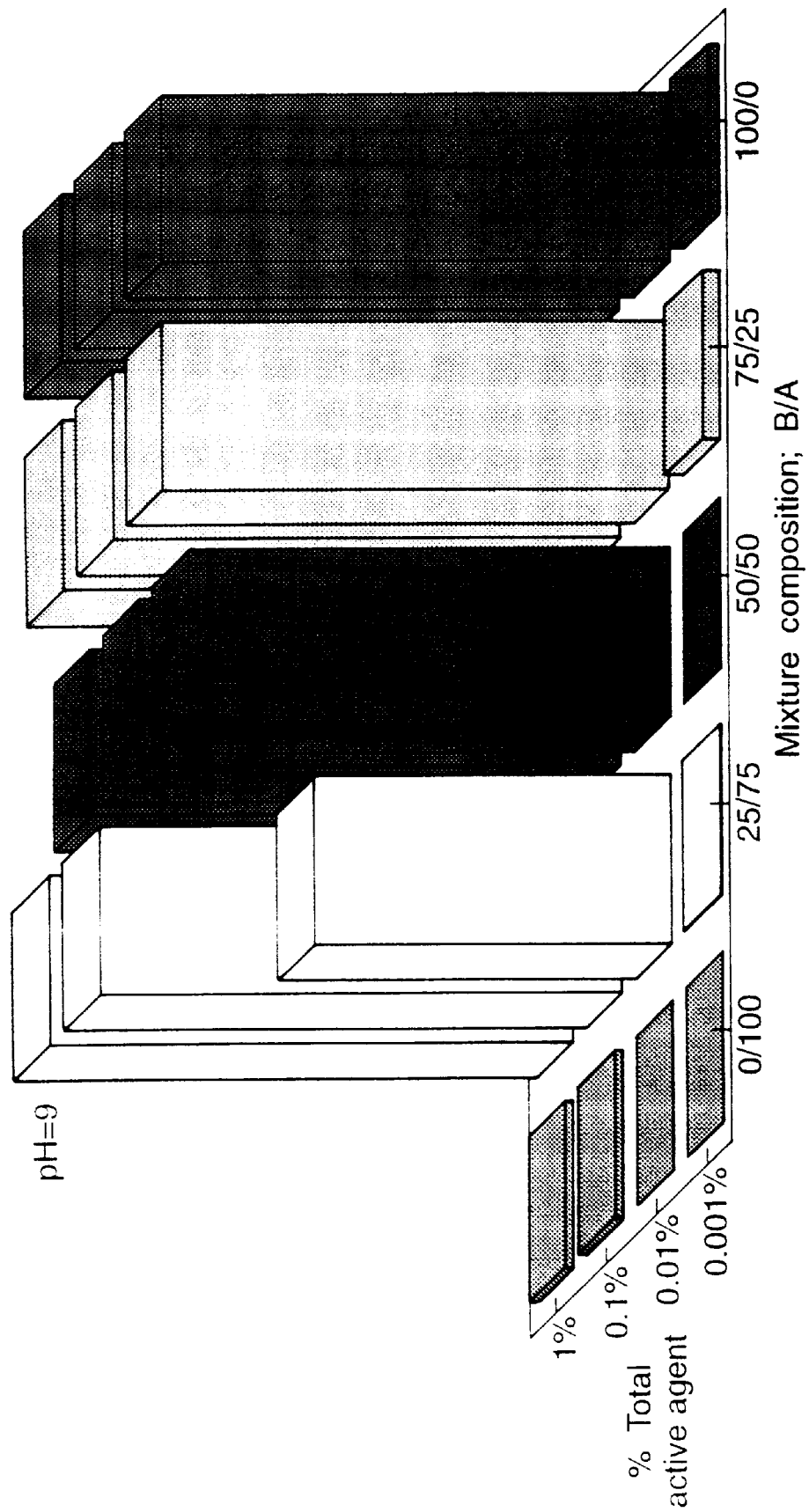

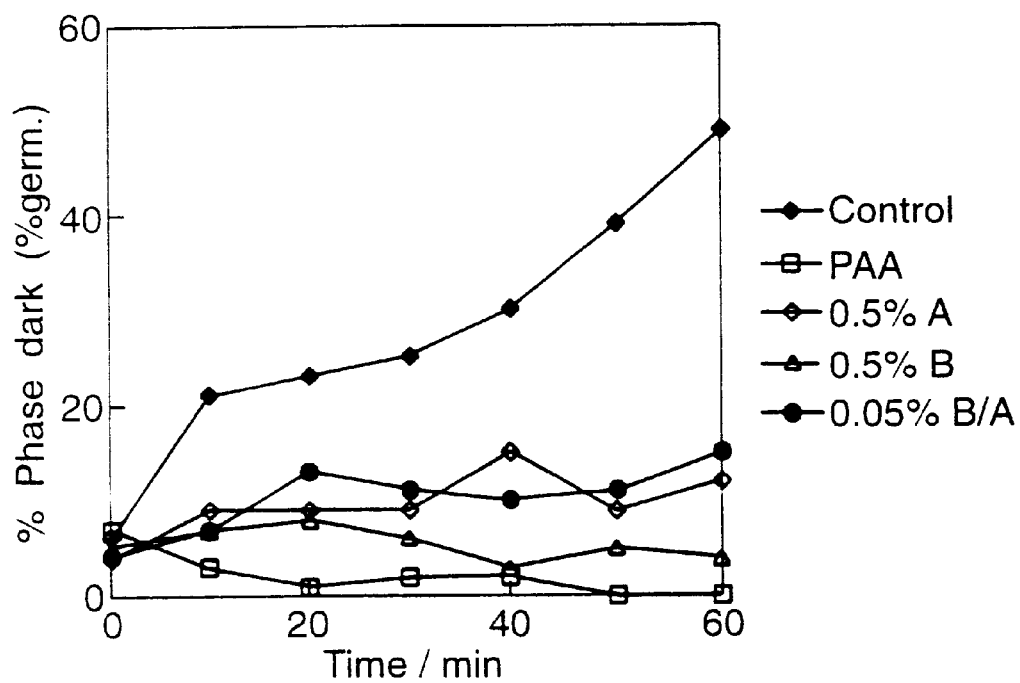

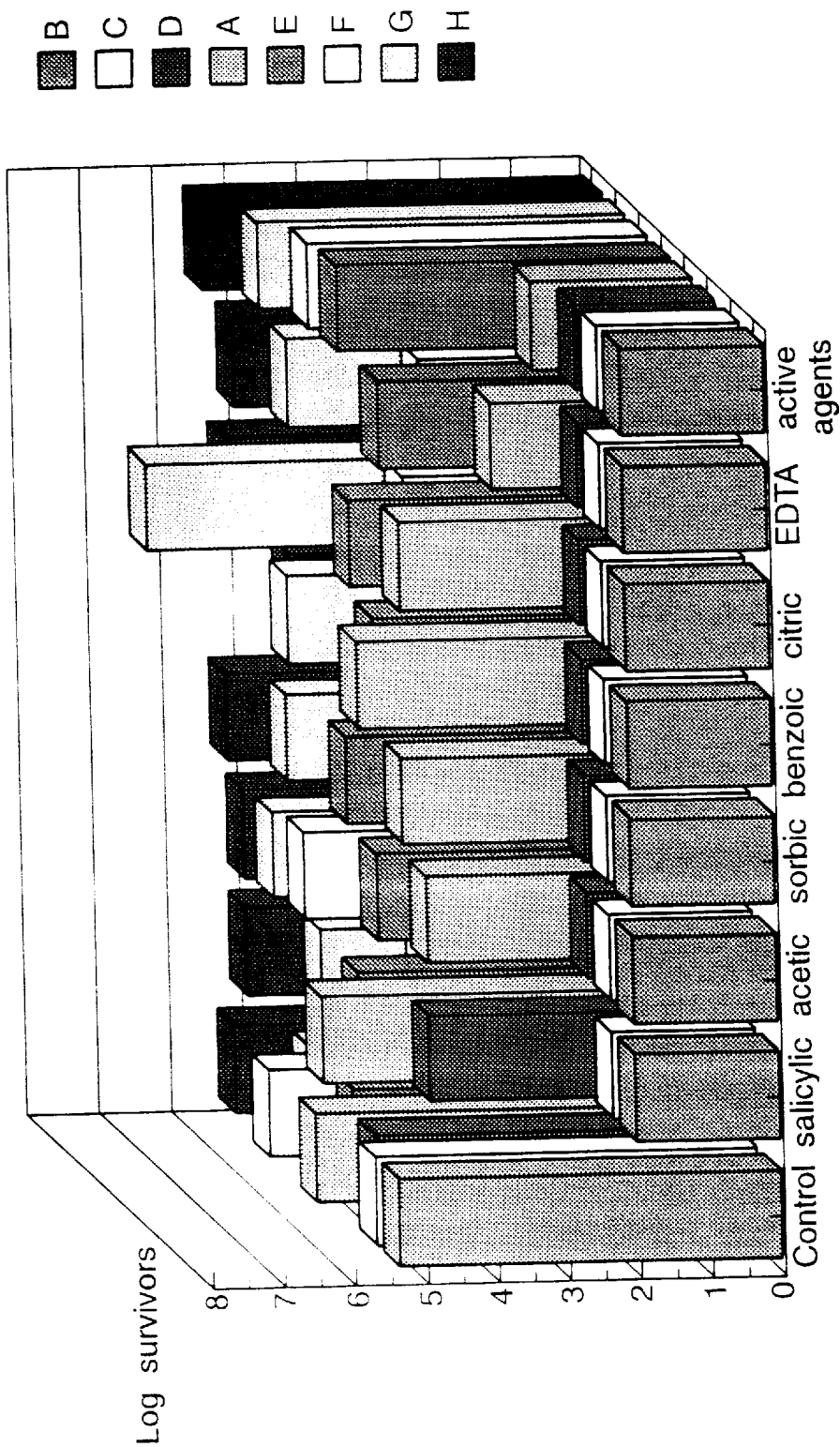

CLEANING AND/OR DISINFECTING COMPOSITION

FIELD OF THE INVENTION

The present invention relates to a cleaning and/or disinfecting composition comprising a tertiary alkyl amine and an alkyl betaine as active agents and to the biocidal use thereof.

BACKGROUND OF THE INVENTION

In order to reduce and prevent infection, to minimize the risk to public health thereof and to prevent product spoilage, disinfectants are commonly used to kill bacteria which spread disease.

A known disinfectant is described in WO 95/00613. However many of the known disinfectants employ environmentally less acceptable and expensive components such as amine oxide, EDTA (Ethylene Diamine Tetra Acetic Acid), and quaternary ammonium compounds.

It is an object of the present invention to yield a cost effective cleaning and/or disinfecting composition which does not employ the above environmentally less acceptable components.

The inventors have found that employing both a tertiary alkyl amine and an alkyl betaine yielded surprisingly good, cost effective biocidal activity at a low active agent concentration, when compared to disinfectants comprising either only a tertiary alkyl amine or only an alkyl betaine.

DEFINITION OF THE INVENTION

According to a first aspect of the present invention there is provided a cleaning and/or disinfecting composition comprising a tertiary alkyl amine and an alkyl betaine. Another aspect of the present invention is concerned with the use of a composition according to the present invention for cleaning surfaces and killing bacteria. cl DETAILED DESCRIPTION OF THE INVENTION A preferred tertiary alkyl amine is 1.3 propanediamine-n-3-aminopropyl. A preferred alkyl betaine is alkyl C9–C15 dimethyl amine betaine.

The tertiary alkyl amine and alkyl betaine comprise preferably 1–15 wt. % of the composition. The cleaning and/or disinfecting composition may furthermore comprise an organic acid or soluble salt thereof, preferably selected from the group consisting of salicylic acid, acetic acid, sorbic acid, benzoic acid, lactic acid, citric acid, malonic acid, tartaric acid, gluconic acid, lactobionic acid, formic acid, malic acid, parabenzoic acid and peracetic acid.

The addition of an organic acid to the composition effects surprisingly good results for killing bacteria, especially gram negative bacteria.

In order to maximize the cleaning effect and to limit the effects of pH change, the composition may furthermore comprise a cleaning agent and a buffer.

The invention will now be illustrated by the following experiments and results, whereby it is noted that:

1) All investigations were carried out using compositions which comprised, as active agents one or more of the following:
   (A) The alkyl betaine, $RN(CH_3)_2CH_2CO_2$; wherein R=3% C10, 70% C12, 25% C14, 2% C16,
   (B) The alkyl amine $RNH(CH_2)_3NH(CH_2)_3NH_2$, wherein R=dodecyl, C12.
   (C) amine oxide; $RN(CH_3)_2O$; R as above
   (D) amine oxide; myristyl dimethylamine oxide
   (E) alkylamphoacetate; alkyl imidazoline betaine
   (F) Coco diethanolamide
   (G) polyoxyethylene sorbitan trioleate
   (H) Coca-amido betaine, $RCONH(CH_2)_3N(Me)_2CH_2CO_2$, R=as above;

wherein the desired pH of the active agents was adjusted using HCl(aq);

2) The percentages of active agents quoted in all the experiments refer to the percentage of total composition;

3) The biocidal effect of the active agents was investigated by the action thereof on the following microorganisms:
   Staphylococcus aureus ATCC 6538 (Gram positive bacterium)
   Pseudomonas aeruginosa ATCC 15442 (Gram negative bacterium)
   Saccharomyces cerevisiae ATCC 9763 (Yeast)
   Bacillus subtilis PSB 357 lux (Spore culture), supplied by Dr P. Hill, Univ. Nottingham; and 4) The first three of these microorganisms were grown in broth at 30° C. for 24 hrs. (bacteria-Tryptone Soya Broth (Oxoid CM129); yeast—"Malt Extract Broth" (Oxoid CM 57). Cultures were then centrifuged at 4000 r.p.m. (Sigma model 3K-1) for 10 minutes, and the cell pellets resuspended on 0.1% peptone water.

Preparation of the B.subtilis Spore Culture

This was grown overnight at 30° C. in heart infusion broth (HIB, Difco) with erythromycin(10 mg/ml) to approximately $1\times10^9$ cells/ml. This was then used to inoculate heart infusion agar(HIA) plates (with 10 mg/ml erythromycin) which were incubated at 30° C. for 7–9 days until 80–100% phase-bright spores were visible under a light microscope. Spores were then harvested by washing the HIA plates with sterile distilled water, followed by centrifugation at 4000 g for 20 minutes at 4° C. The spores were washed three times by centrifugation and resuspensed in sterile distilled water, before being pasteurized at 70° C. for 40 minutes. Finally, the spores were resuspended in distilled water containing erythromycin (10 mg/ml) and stored at −80° C.

To stimulate spore germination, 100 $\mu$l of the thawed suspension was heat activated, at 70° C. for 30 minutes. 40 $\mu$l of the heat activated spores was added to a solution (30° C.) of NBLi (138 $\mu$l) and sterile distilled water (20 $\mu$l). Samples were removed from the 30° C. water bath every ten minutes and the percentage phase dark enumerated.

BRIEF DESCRIPTION OF THE FIGURES

FIGS. 3–13 show effects of acid mixtures.
Investigation into the Biocidal Effect of (A), (B) and (A):(B) Mixtures on the First Three Micro-organisms To investigate the effect of the agents on the first three microorganisms (S.aureus, P.aeruginosa and S.Ceresiviae) the following suspension test was used to determine the log reduction of the micro-organisms in all experiments.

Figure 1:
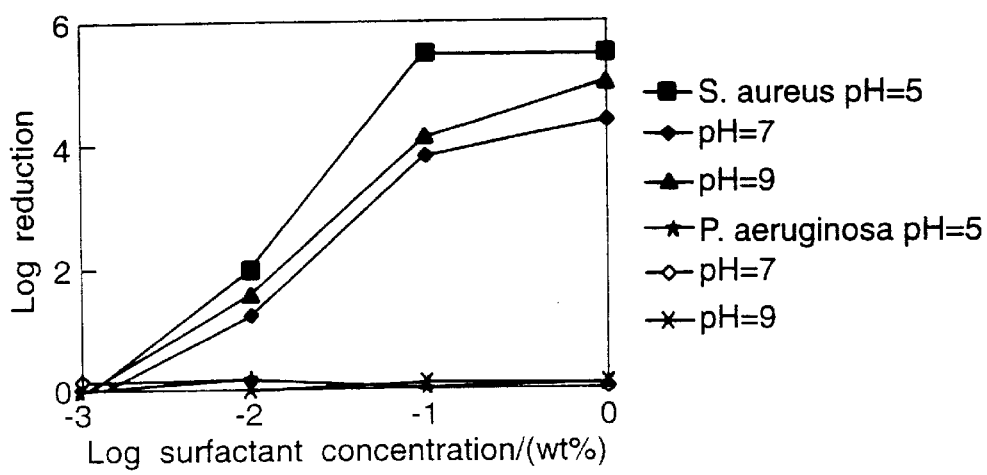
FIGS. 1 and 2 show pH effects.

The microorganism suspension (0.1 ml) was added to the test agent (10 ml) and mixed thoroughly and left at ambient temperature for five minutes. Following the contact time, an amount (1 ml) was transferred to Universal Quenching Agent (9 ml), peptone (1 g), Tween80 (5 g), sodium thiosulphate (1 g) and lecithin (0.7 g) per liter of deionized water)) to inactivate the disinfectants. Survivors were counted following serial dilution in 0.1% peptone water on appropriate agar using 0.1 ml spread plates. The plates were incubated at 30° C. for 48 hours. The log reduction of the microorganisms was then calculated.

EXPERIMENT 1

Figure 2:
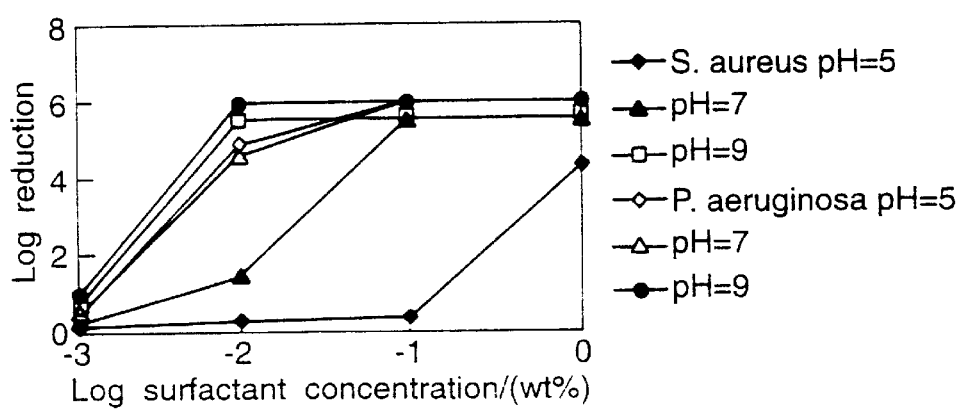

Investigation into the effect on S.aureus and P.aeruginosa when treated with (A) and (B) respectively after a five minute contact time, at a pH between pH=5 and pH=9, the results of which are graphically shown in FIGS. 1 and 2.

Conclusions from FIGS. 1 and 2:

At pH's of 5 to 9 (A) was effective against the Gram positive bacterium, S.aureus. At lower concentrations of (A), the lower pH solutions were more effective biocides against this organism.

(B) was effective against the gram negative bacterium P.aeruginosa. However (B) was ineffective at low pH except at high concentrations against the gram positive bacterium S.aureus.

For both (A) and (B), a concentration of 0.01% recorded over five log reductions in the bacteria (kills) at pH=9. At pH=7 only 1.5 log reductions were observed and a very small reduction at pH=5. At the 0.1% level and at all pH values examined there was greater than log 5 kill with P.aeruginosa. At 0.01% and pH=9 greater than log 5 kill was observed whereas at pH of 7 and 5, only a log reduction of 4.5 was recorded.

EXPERIMENT 2

Figure 3A:
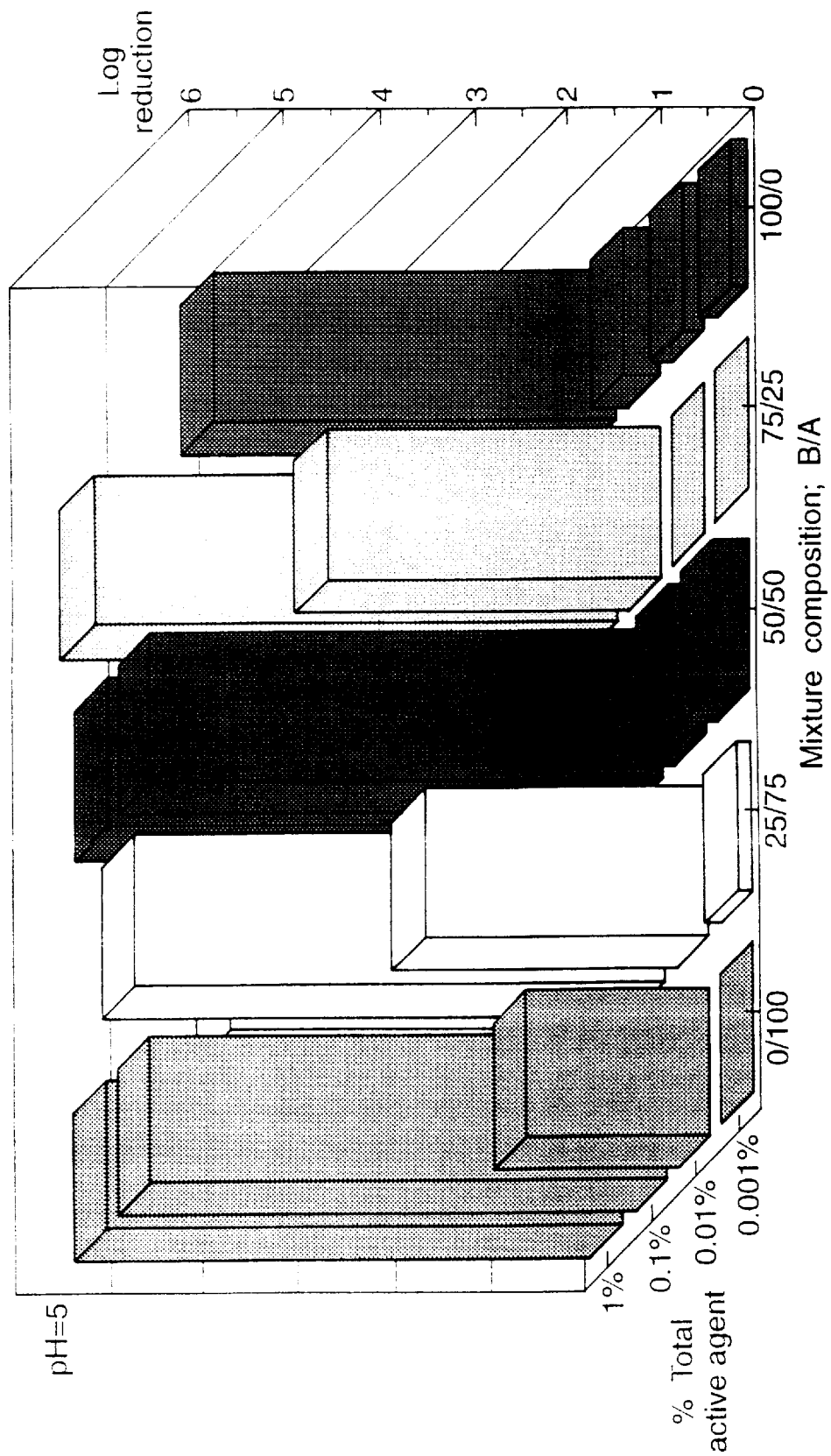
Figure 4A:
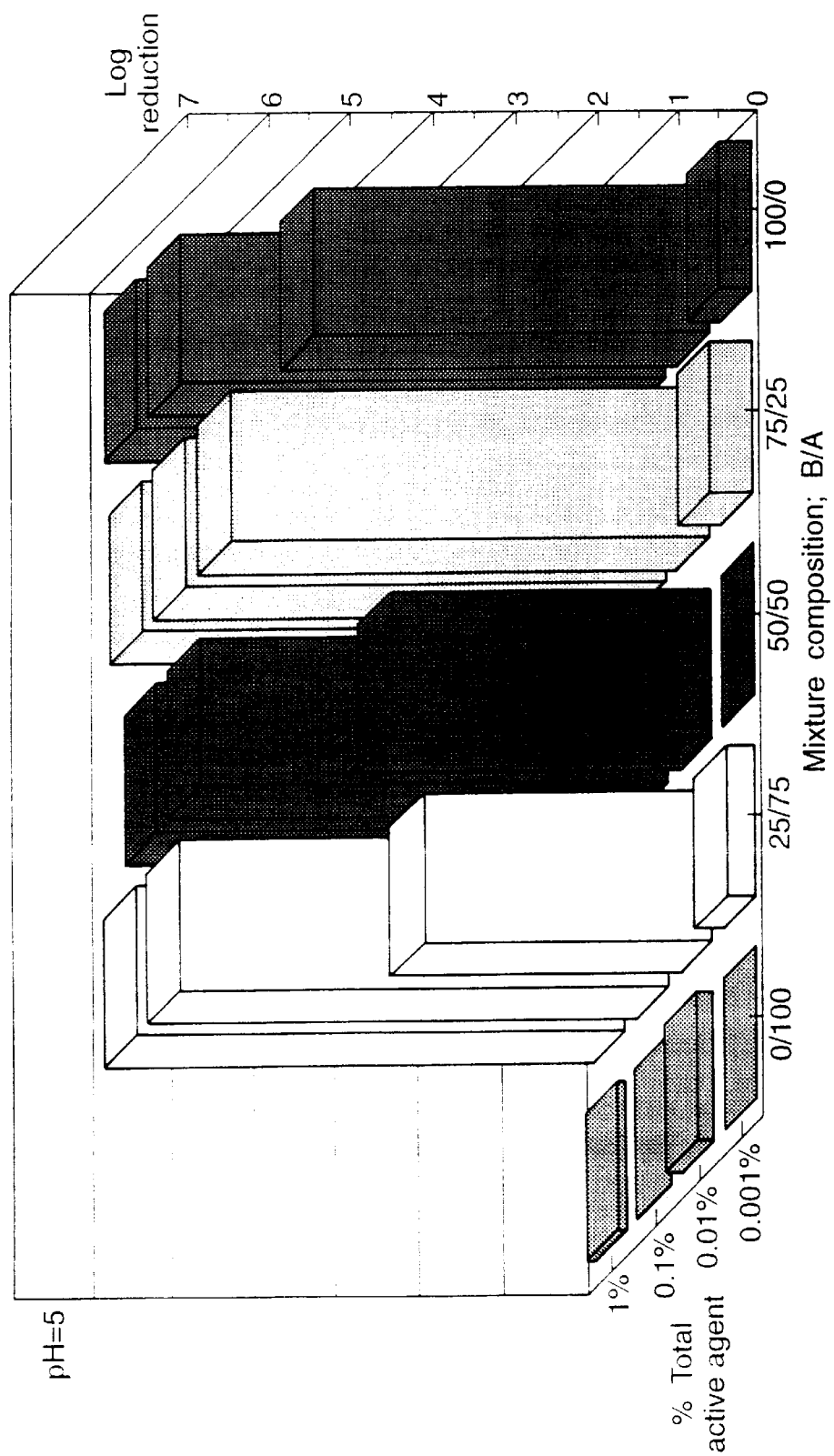
Figure 4B:
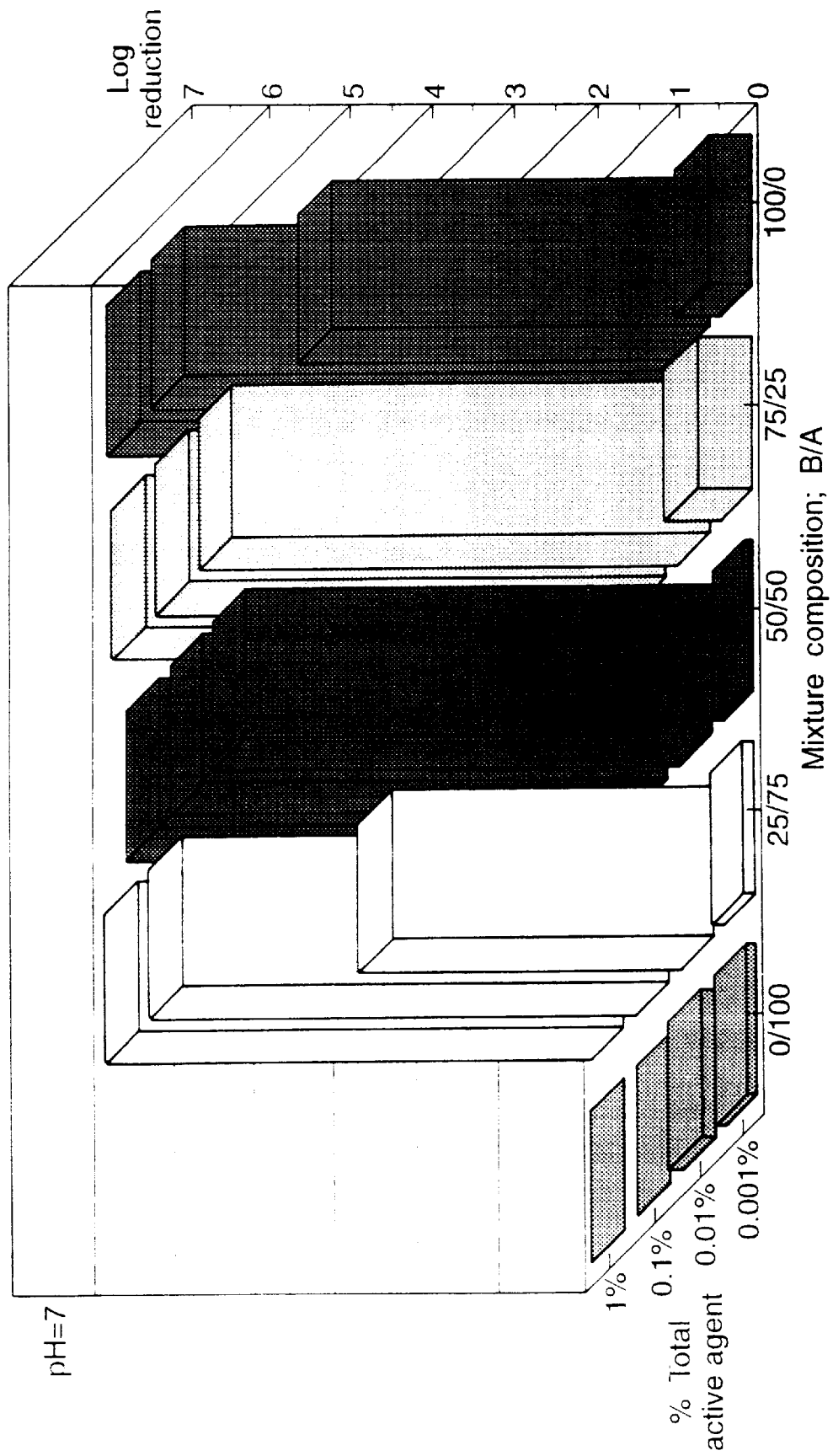
Figure 4C:
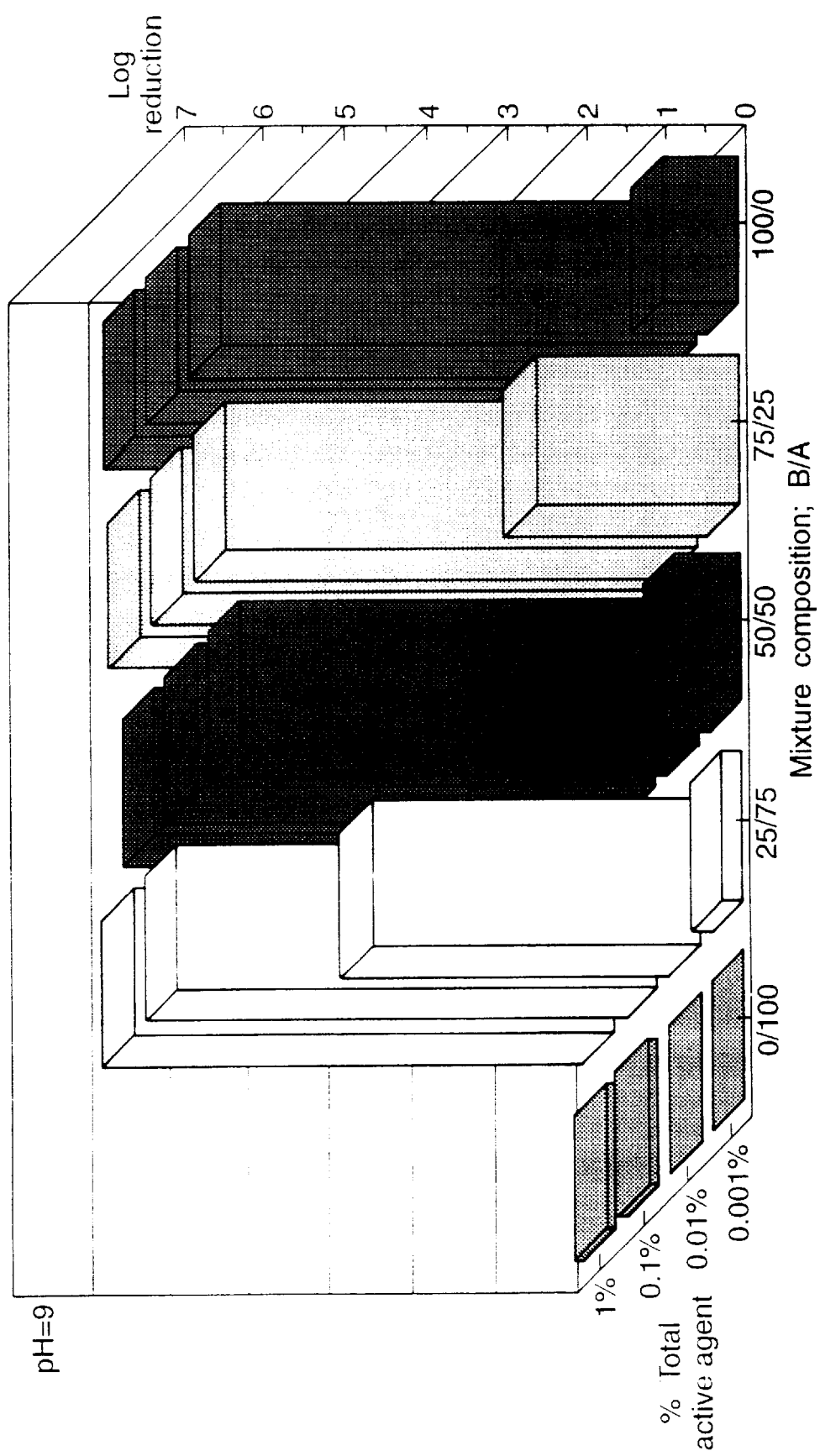

FIGS. 3a, b and c and FIGS. 4a, b and c respectively show the effect of mixtures of the active agents (A) and (B), and pH on the log reduction of S.aureus and P.aeruginosa.

Figure 3B:
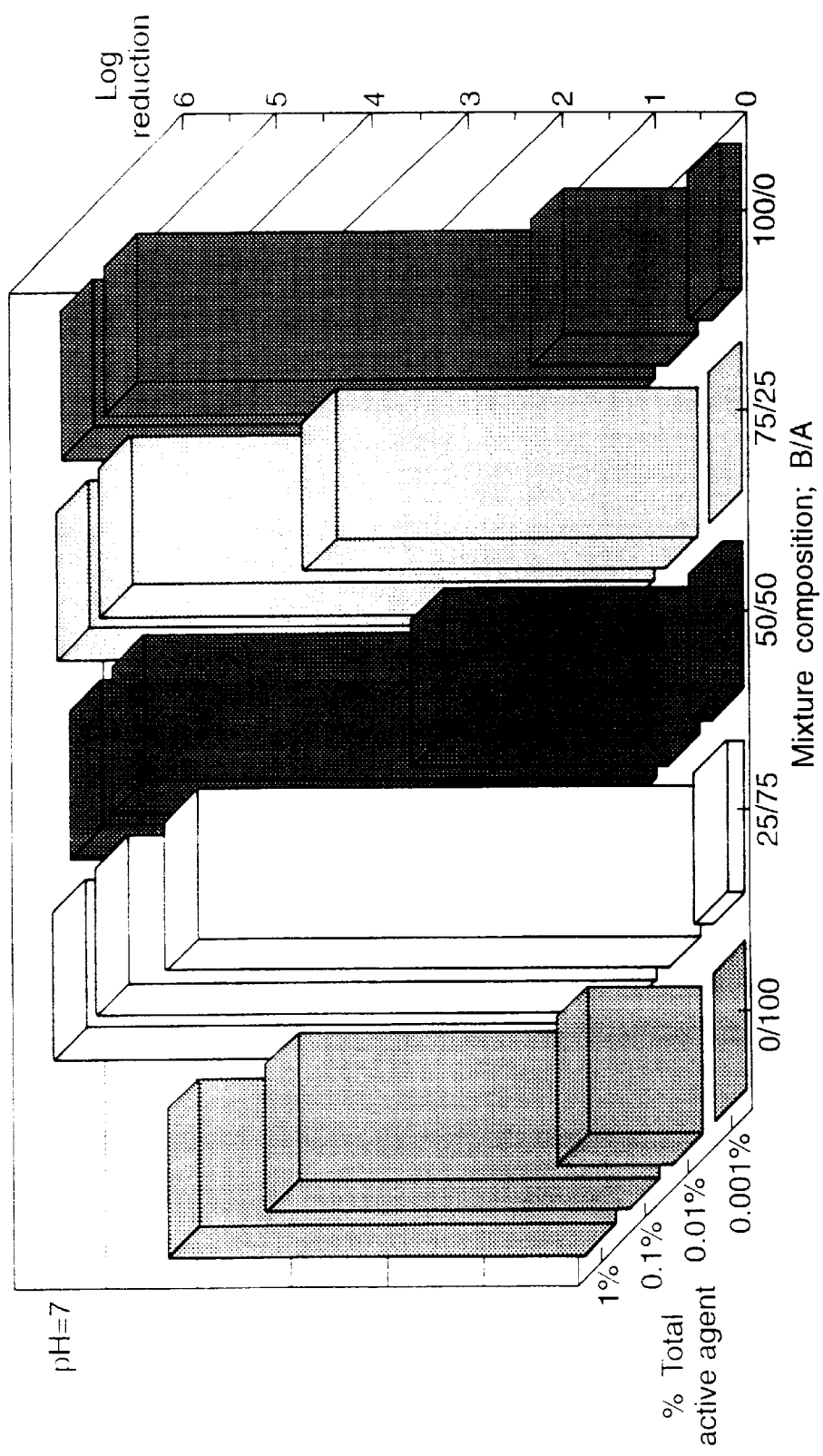

Conclusions from FIGS. 3(a,b,c) and 4(a,b,c):

FIG. 3a shows that, as the mix changes to more (B), at pH=5, a higher concentration of total active agent is required to yield a satisfactory log reduction. As the pH was raised, the total amount of active agent required to effect >log 5 reduction, decreases. At pH=9, FIG. 3c, the effect of (B) appears to outweigh the activity of (A). However at pH=7, the 25:75 and the 75:25 (B):(A) compositions appear to have acted in a synergistic way. FIGS. 4a, b and c show that at pH=5 as the amount of (B) increases, a steady progression of increasing log reduction is observed which peaks at the 75:25 mixture. This effect is reflected in the graphs at pH=7 and pH=9. At a concentration of 0.001% active, the 75:25 mixture achieves nearly 3 log reductions and total kill at the 0.01% level at pH=9.

EXPERIMENT 3

Figure 5A:
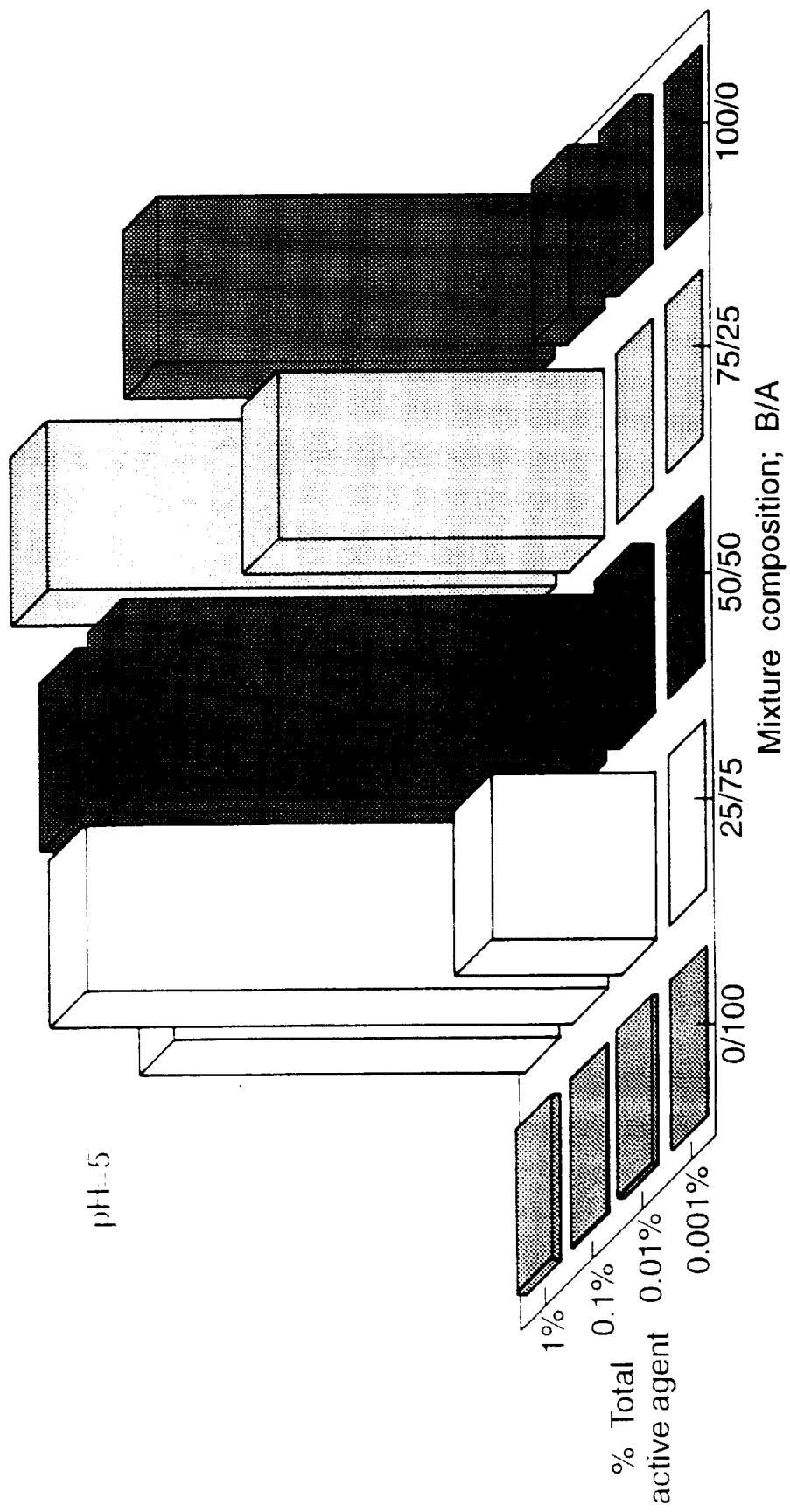

The inventors then carried out research to optimize the mixture in order to improve the log reductions in both organisms. This was done by multiplying the log reductions for each of the organisms and plotting this against the concentration and percentage composition wherein the highest point reached on graphs represented the theoretical mixture best able to deal with both organisms. Such graphs are shown in FIGS. 5a, b and c, for the three pH values examined. (Note this was done by the inventors purely for graphical demonstration, the multiplying of two logs in this manner is not related to any known physical phenomenon).

Conclusions from FIGS. 5(a,b,c):

At pH=5, the theoretical optimum compositions against the bacteria S.aureus and P.aeruginosa were the 25:75 and the 50:50 mix of (B):(A) at 0.1% total active agent in the mixture composition. The 25:75 mix gave a better log reduction at 0.01% total active agent in the composition. At pH=7, the 25:75 or the 75:25 appeared to be suitable and could be used at the 0.01% level. At pH=9, the 50:50, 75:25 and the 100% (B) compositions gave the best results.

EXPERIMENT 4

An examination of the 50:50 (B):(A) mixture was conducted at a variety of concentrations against S.cerevisiae. A plot of log reduction is shown in FIG. 6.

Figure 6:
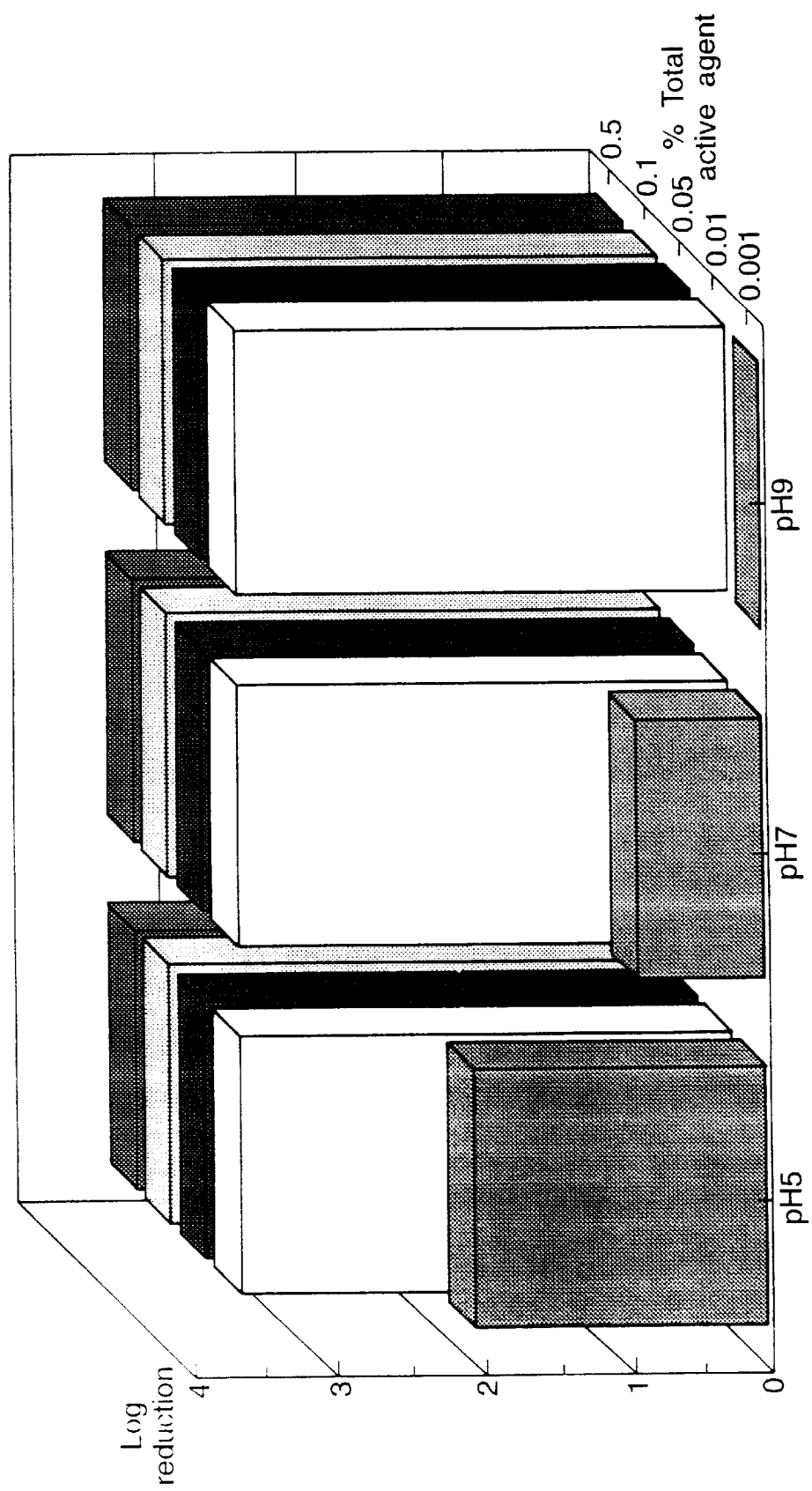

Conclusions from FIG. 6:

Unlike the bacteria examined, the yeast showed a decrease in biocidal effect as pH was increased at the lowest concentrations of active agent used. With this mixture composition, 0.01% of active agent gave a total kill of the yeast at all pH values examined.

Investigation Into the Comparative Effect of Disinfecting Compositions, Comprising the Above Active Agents (A)–(H) on the Three Organisms at a pH of 5.0 and Various Active Agent Concentrations. (Experiments 5–7)

EXPERIMENT 5

Effect of active agents on S.aureus At 0.5% levels, the ability to reduce the levels of organisms showed the following activity:

(A)>(C)>>(B)>(D)>(E)>(G)=(F)=(H)=Control

EXPERIMENT 6

Effect of active agents on P.aeruginosa At 0.5% levels, the ability to reduce the levels of organisms showed the following activity:

(B)=(C)>(D)>>(E)>(G)=(A)=(F)=(H)=Control

EXPERIMENT 7

Effect of active agents on S.cerevisiae At 0,5% levels, the ability to reduce the levels of organisms showed the following activity:

(B)=(C)=(D)>(A)>>(E)=(F)>(G)=(H)=Control

Figure 7A:
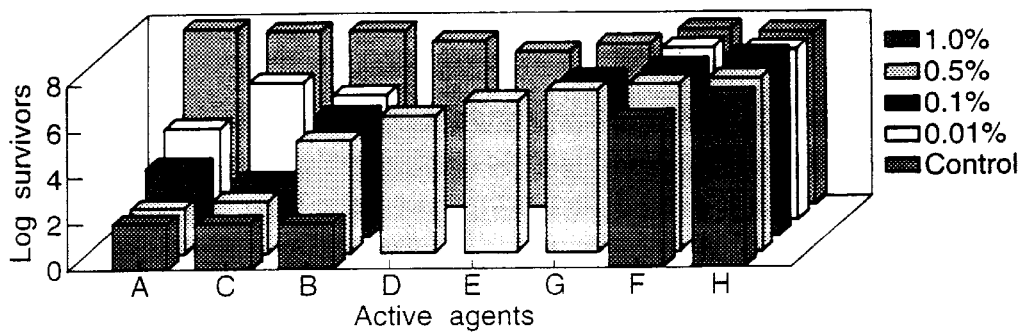
Figure 7B:
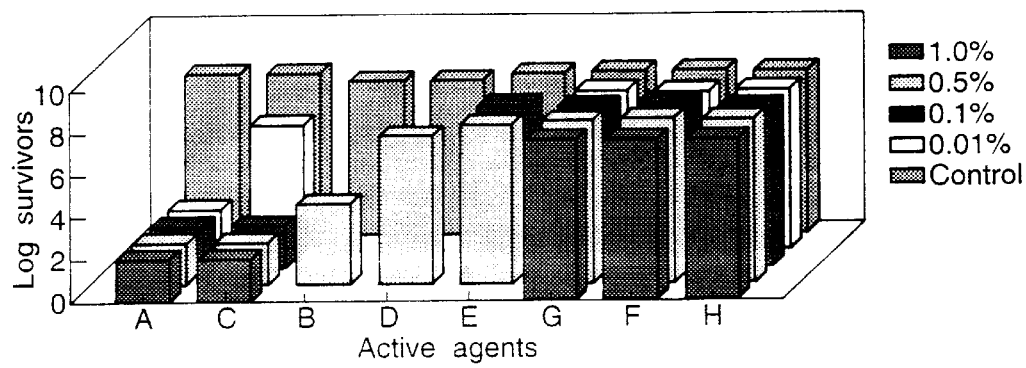
Figure 7C:
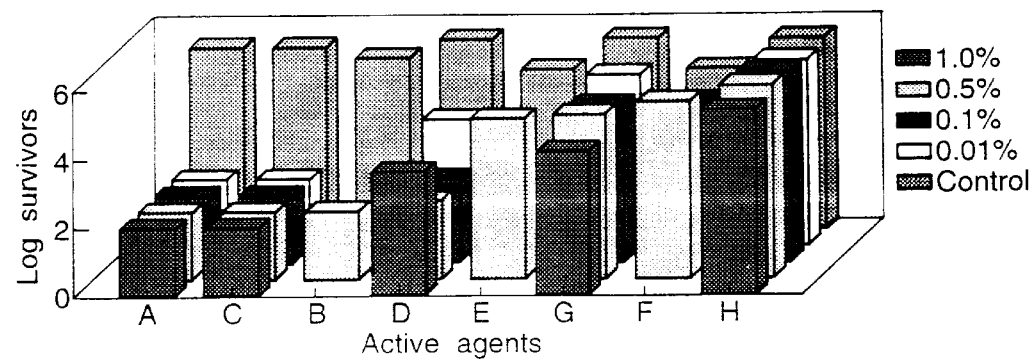

FIGS. 7a, b and c show the comparative effect of the 8 active agents used in this study on the organisms in experiments 5, 6 and 7, respectively.

Conclusions from FIGS. 7a, b and c:

At a pH of the test (pH=5), (B) is considered to be a cationic surfactant, and as such it was to be expected that good activity against gram positive bacteria would be achieved. However, this was not the case (see FIGS. 9a, b and c). The inventors believe that at this pH there may be a chemical reaction between the surfactant and the techoic acids of the murein layer of the bacteria. This essentially makes the surfactant unable to act as a biocide. At higher concentrations this is circumvented as the layer is swamped with the surfactants.

Investigation Into the Effect of (B) and (A) on Spore Germination of S.cerevisiae (Experiment 8):

Background

Spores can be likened to an armor plated bacterium. As such they are much more difficult to kill than a normal, vegetative cell. Normal disinfectants and levels used do not readily kill bacterial spores. After cleaning, bacterial spores can therefore cause contamination problems if they germinate and multiply. One strategy for inactivating bacterial spores is to germinate them into the more sensitive vegetative form; In Tyndalisation, spores are heated and cooled repeatedly, the heating cycle stimulates the spores to germinate into the vegetative (easy to kill) state. The next heating cycle kills the germinated bacteria and induces another batch of spores to germinate and so on.

It has been shown that known disinfectants comprising quaternary ammonium compounds (QACs) are not effective sporicides. Apparent sporicidal activity is due to the QACs sticking to the spores. Upon germination, the locally high concentration of biocide kills the bacterium. However, repeated washing or using universal quenching agent allows recovery, because the biocide is removed.

The term "chemical germination" was coined to summarize the germination-like changes induced in spores by active agents.

Experimental

Active agents (A) and (B) were mixed with the *Bacillus subtilis* spores, in the following composition concentrations:
- (A) 0.5%
- (B) 0.5%
- (A):(B) 0.05%

FIG. 8 shows the results of this.

Peracetic acid a known sporicide, was used as a positive control.

Results and conclusions from FIG. 8:

- (B) at 0.5%: Inhibition of germination occurred and was greater than that of (A) alone.
- (A) at 0.5%: Inhibition of germination occurred and was lesser than that of (B) alone.
- (B):(A) mixture
  0.05%: Inhibition of germination occurred, to a lesser degree than (A) or (B) alone.

The inventors postulate that as the spores germinate the active agents present on the spore coats kill the vegetative cells.

Investigation Into the Possible Synergistic Effects of the Active Agent Mixtures (B):(A).

(EXPERIMENTS 9–11)

Solutions of (B):(A), in a ratio of 1:3 at total active agent concentrations of the solution compositions from 0.002 to 0.01% were prepared. Separate solutions of (B) and (A) alone were also made up at the same total active agent concentrations.

The following tables (1–3) give the results of examples in terms of total composition, and compare the calculated, expected additive effect with the experimentally derived effect, carried out at a pH of 9.

EXPERIMENT 9

Effect of a (B):(A), (1:3) mixture on *S.aureus*

The results of this example are shown below in Table 1.

TABLE 1

| Total active agent/% | (B)/% | (A)/% | Expected (Additive) effect log reduction | Actual effect log reduction |
|---|---|---|---|---|
| 0.01 | 0.0025(2)a | 0.0075(0.9)a | 2.9 | >5.3 |
| 0.008 | 0.002(1.34) | 0.006(0.01) | 1.35 | >5.3 |
| 0.006 | 0.0015(1) | 0.0045(0) | 1 | 3.4 |
| 0.004 | 0.001(1) | 0.003(0) | 1 | 1 |
| 0.002 | 0.0005(0) | 0.0015(0) | 0 | 0.08 | a(x) denotes log reduction of pure surfactant at that concentration

EXPERIMENT 10

Effect of a (B):(A), (1:3) mixture on *P.aeruginosa*

Table 2, below, shows the results of this example.

TABLE 2

| Total active agent/% | (B)/% | (A)/% | Expected (Additive) effect log reduction | Actual effect log reduction |
|---|---|---|---|---|
| 0.01 | 0.0025(5.3)a | 0.0075(0)a | 5.3 | >5.5 |
| 0.008 | 0.002(4.98) | 0.006(0) | 4.98 | >5.5 | a(x) denotes log reduction of pure surfactant at that concentration

EXPERIMENT 11

Effect of a (B):(A) (1:3) mixture on *S.cerevisiae*

Table 3, below shows the results of this example.

TABLE 3

| Total active agent/% | (B)/% | (A)/% | Expected (Additive) effect log reduction | Actual effect log reduction |
|---|---|---|---|---|
| 0.01 | 0.0025(4.5)a | 0.0075(1.4)a | 5.9 | >5.5 |
| 0.008 | 0.002(3.31) | 0.006(1.22) | 4.53 | >5.5 | a(x) denotes log reduction of pure surfactant at that concentration

Conclusions from tables 1–3:

These tables show that a greater effect is achieved than was to be expected by simply mixing (A) and (B).

Investigation to Determine the Concentration of Active Agent (B), (A), and Mixtures Thereof, in the Composition, Required to Achieve a Log Four Reduction in *S.aureus* and *P.aeruginosa* Respectively. (Experiments 12–15):

EXPERIMENT 12

Effect of (A) and (B) on *S.aureus*

Table 4, below shows the results of this example.

TABLE 4

| | pH | | |
|---|---|---|---|
| | 5 | 7 | 9 |
| (A) | 0.1% | 0.1% | 0.1% |
| (B) | 1% | 0.1% | 0.01% |

EXPERIMENT 13

Effect of (A) and (B) on *P.aeruginosa*

Table 5 below shows the result of this experiment.

TABLE 5

| | pH | | |
|---|---|---|---|
| | 5 | 7 | 9 |
| (A) | >1% | >1% | >1% |
| (B) | 0.01% | 0.01% | 0.01% |

EXPERIMENT 14

Effect of mixtures of (A) and (B) on *S.aureus*

Table 6 below, shows the results of this experiment.

TABLE 6

| | pH | | |
|---|---|---|---|
| (B):(A) ratio | 5 | 7 | 9 |
| 25:75 | 0.1% | 0.01% | 0.01% |
| 50:50 | 0.1% | 0.1% | 0.01% |
| 75:25 | 1% | 0.01% | 0.01% |

EXPERIMENT 15

Effect of mixtures of (A) and (B) on *P.aeruginosa*

The results of this experiment are shown below in table 7

TABLE 7

| | pH | | |
|---|---|---|---|
| (B):(A) ratio | 5 | 7 | 9 |
| 25:75 | 0.1% | 0.01% | 0.01% |
| 50:50 | 0.01% | 0.01% | 0.01% |
| 75:25 | 0.01% | 0.01% | <0.01% |

Conclusions from tables 4–7:

These tables show that when mixed, the potency of the disinfecting composition, comprising a (B):(A) mixture is greater than would be expected from combining (B) and (A).

Investigation Into the Biocidal Activity of Organic Acids in Combination with a Cleaning/Disinfectant Composition Comprising One or More of the Active Agents (A)–(H), (Experiment 16):

Background

Weak acids are antimicrobial[1], however, the extent of their antimicrobial ability is dependent on several factors which include the pH of the solution, the pKs of the acids and their permeabilities or partitioning ability. Lauric acid is a moderately good anti-microbial material, it is able to partition itself into microbial membranes, become ionized and release the proton; the proton disrupts proton-gradients, the fatty acid anion can disrupt transport processes and can help permeabilise membranes. However this effect is based on the protonated material, as such its ability as an antimicrobial is lost as the pH of the outside medium is raised to pHs beyond the pK, i.e. as the acid becomes more ionized. To take advantage of the weak acid effect low pH solutions should be used. However, low pH solutions (pH<<5) can be corrosive on certain surfaces and are preferably avoided.

EXPERIMENT 16

A range of weak acids, see following tables and figures, was exposed to the three test organisms:

*Staphylococcus aureus* ATCC 6538

*Pseudomonas aeruginosa* ATCC 15442

Figure 9:
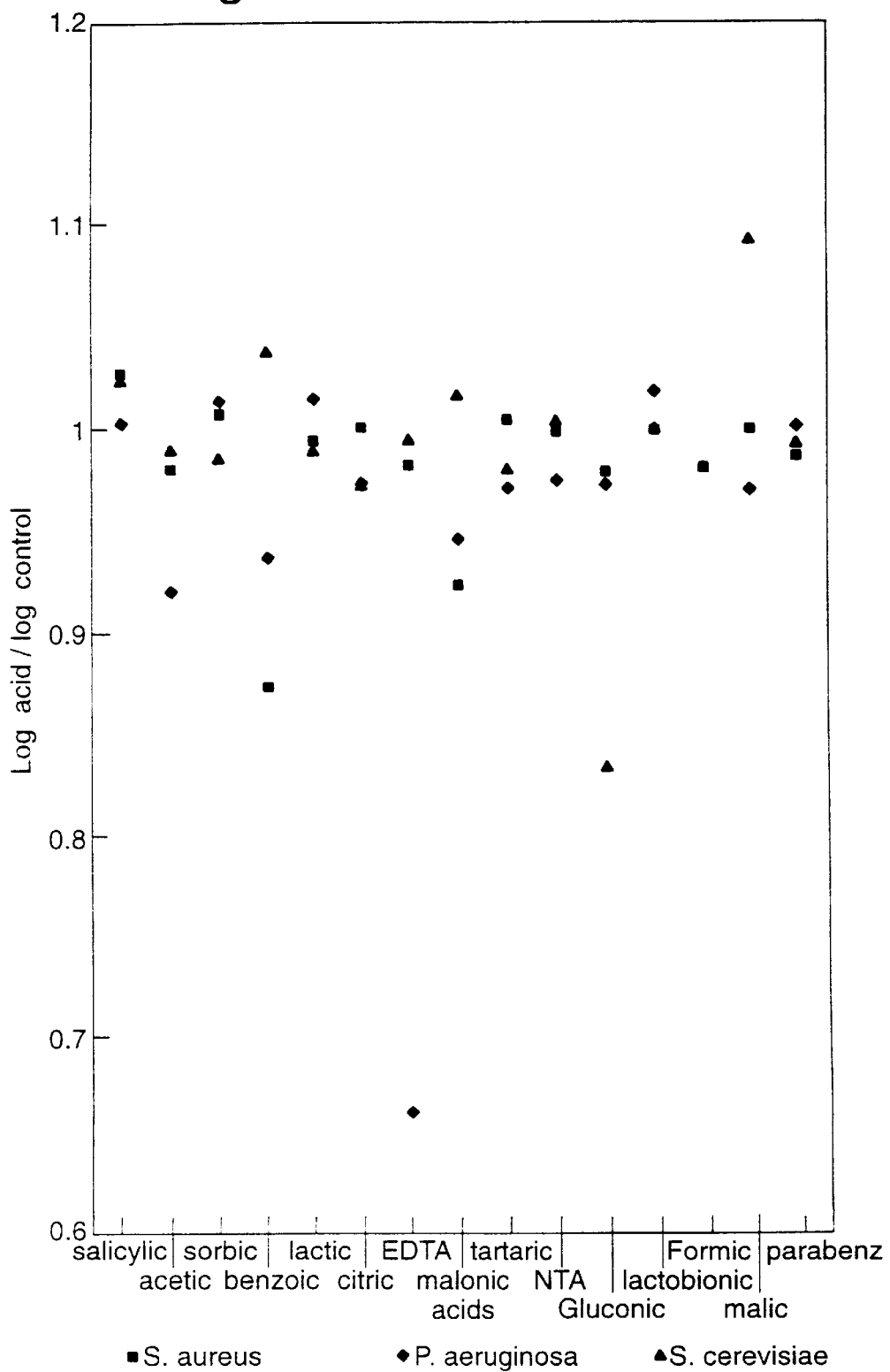

*Saccharomyces cerevisiae* ATCC 9763, at a concentration of 0.5% by weight and the effects recorded according to the suspension test. FIG. 9 shows the results of experiment 16, a plot of the ratio of the log survivors for the test acid versus a water control.

Conclusions from FIG. 9:

A ratio of log acid:log control greater than the suggested that the acid acted as a growth promoter, less than one an inhibitor.

Investigation Into the Effect of Disinfectant Compositions, Comprising Mixtures of the Active Agents with Acids on the First Three Organisms. (Experiments 17–19)

Figure 10A:
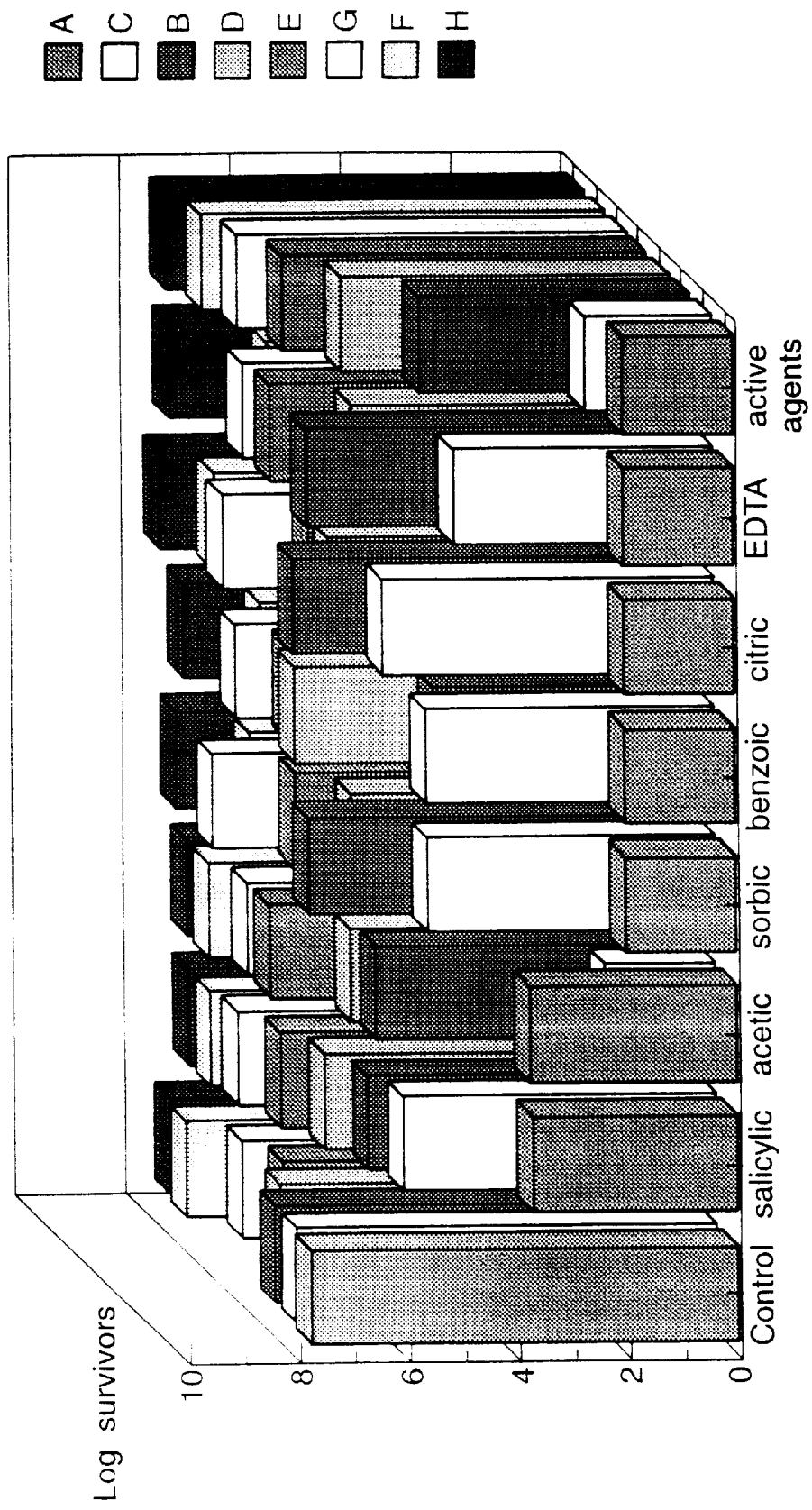

FIGS. 10*a*, *b* and *c* show the results of the experiments 17–19 into the effect of mixtures of active agents (A)–(H) and the acids, salicylic, acetic, sorbic, benzoic, citric, EDTA on the three microorganisms, at a concentration of 0.5% by weight of the active agent, as carried out by the suspension test.

The pH of the disinfecting compositions was adjusted to pH=5 with HCl and NaOH.

EXPERIMENT 17

Effect on *S.aureus* (FIG. 10*a*).

Conclusions from FIG. 10*a*:

The most surprising effect observed was the antagonistic effect of (A) with salicylic acid. In general all the acid/surfactant mixtures examined were antagonistic.

EXPERIMENT 18

Figure 10B:
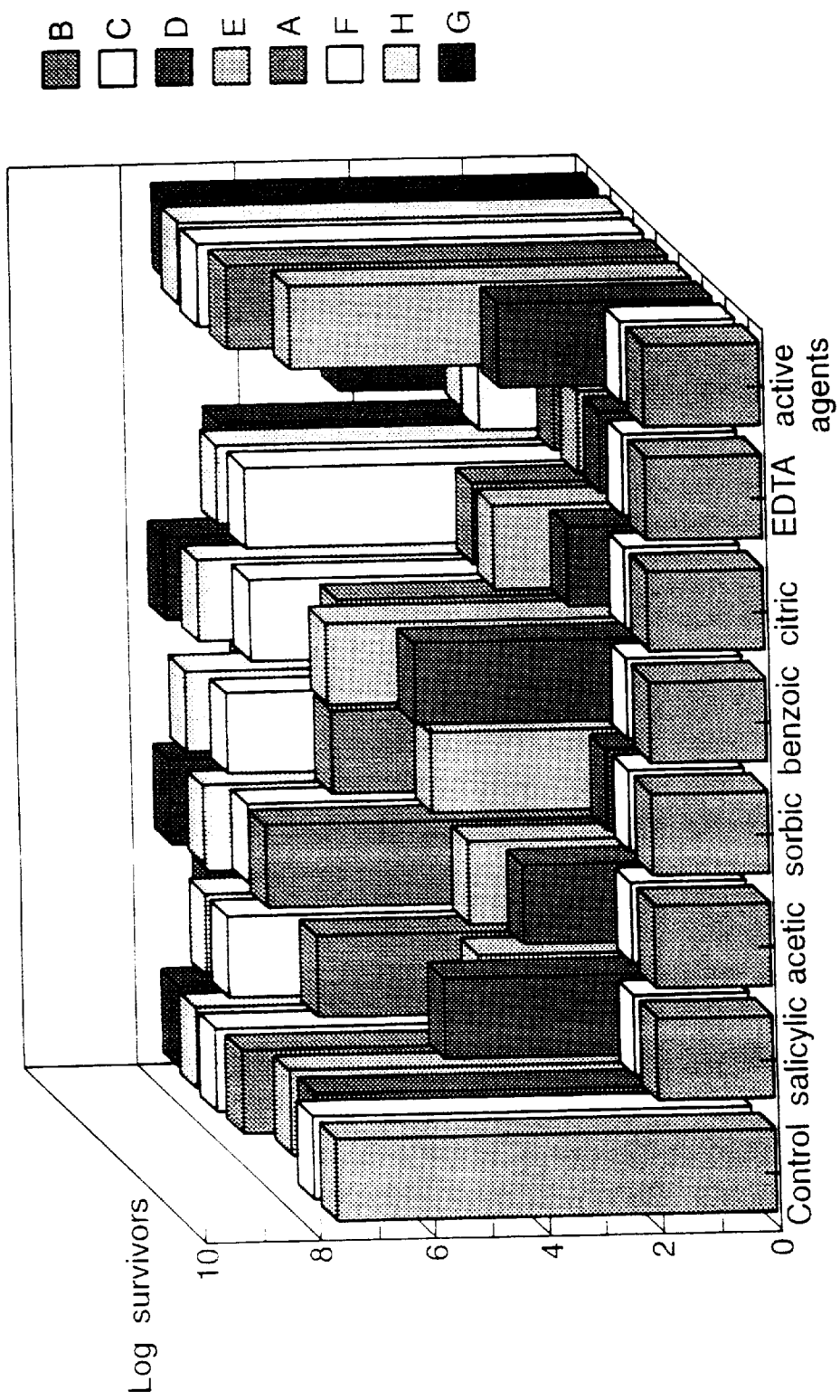

Effect on *P.aeruginosa* (FIG. 10*b*).

Conclusions from FIG. 10*b*:

In general there was an improvement in the kill when an acid was present.

EXPERIMENT 19

Effect on *S.cerevisiae* (FIG. 10*c*)

Conclusions from FIG. 10*c*:

The addition of citric acid at pH=5 gave a large synergistic killing effect on gram negative bacteria when mixed with (A).

As was shown above, (A) cannot kill gram negatives by itself, (see FIG. 1, experiment 1).

However the addition of citric acid improved its log reduction from zero to log four reduction, which is surprising.

Furthermore citric acid at pH=5 at the level used (0.5%) did not affect the growth of the bacteria,(see FIG. 8).

Investigation Into the Biocidal Effect of Different (A):acid Mixtures Concentrations on the Microorganisms (Experiments 20–22)

(In the experiments 20–28, the % of the active agent and the acid by weight in the composition were in all cases equal.)

Figure 11A:
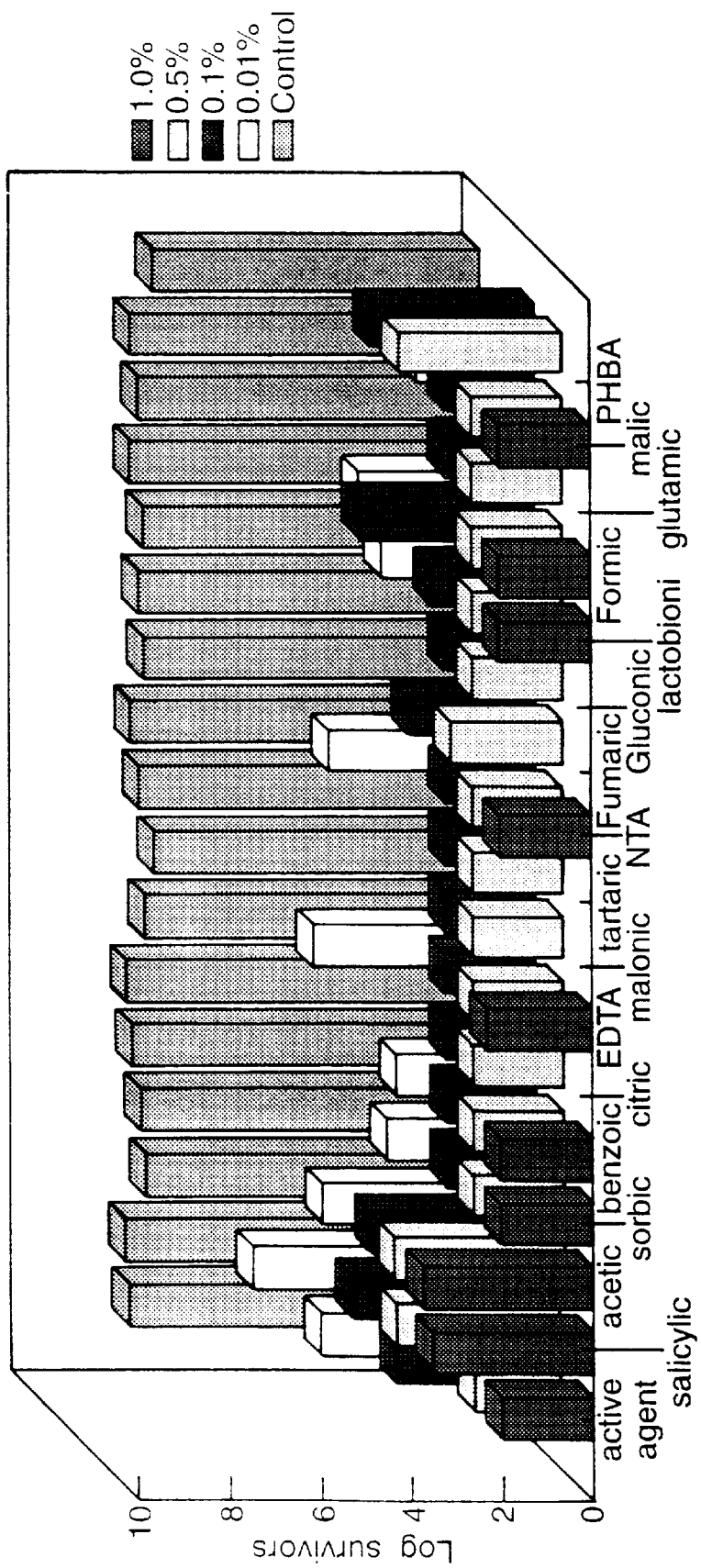

FIGS. 11*a*, *b* and *c* show the results of the experiments 20–22 into the effect of different concentrations (0.01%–1.0%) of the (A):acid mixtures against the three micro-organisms.

EXPERIMENT 20

Effect on *S.aureus*, FIG. 11*a*.

EXPERIMENT 21

Figure 11B:
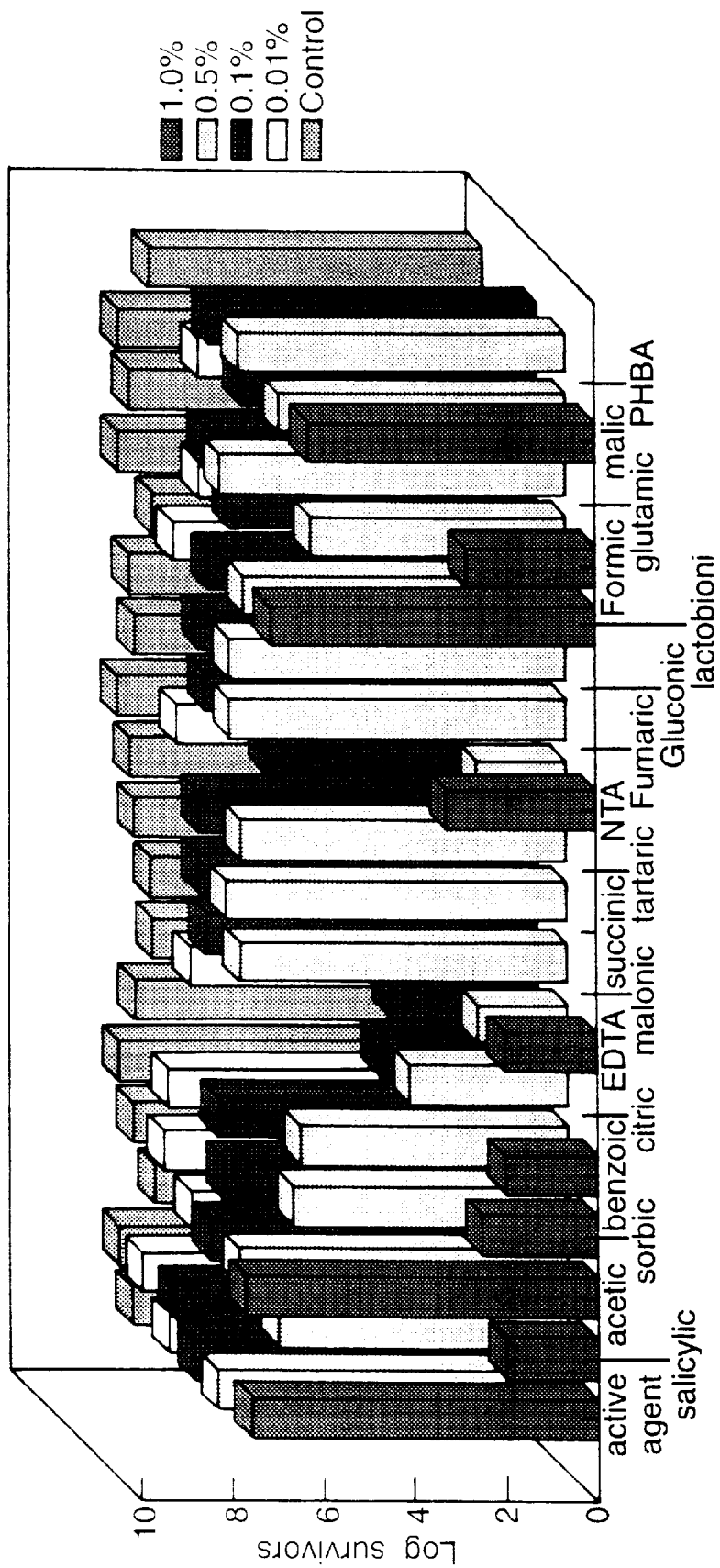

Effect on *P.aeruginosa*, FIG. 11*b*.

EXPERIMENT 22

Figure 11C:
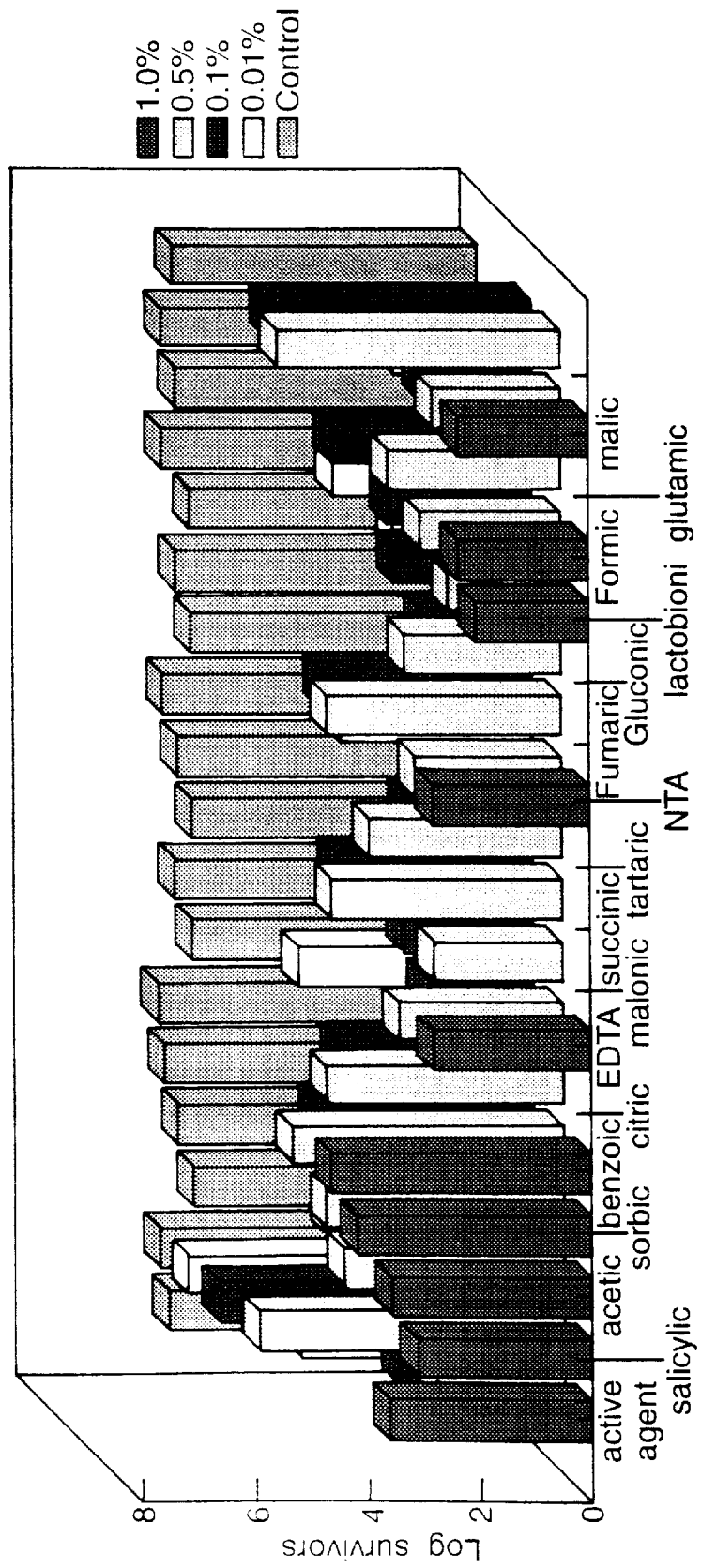

Effect on *S.cerevisiae*, FIG. 11*c*.

Investigation Into the Biocidal Effect of Different (B):acid Mixture Concentrations on the Microorganisms, (Experiments 23–25)

Figure 12A:
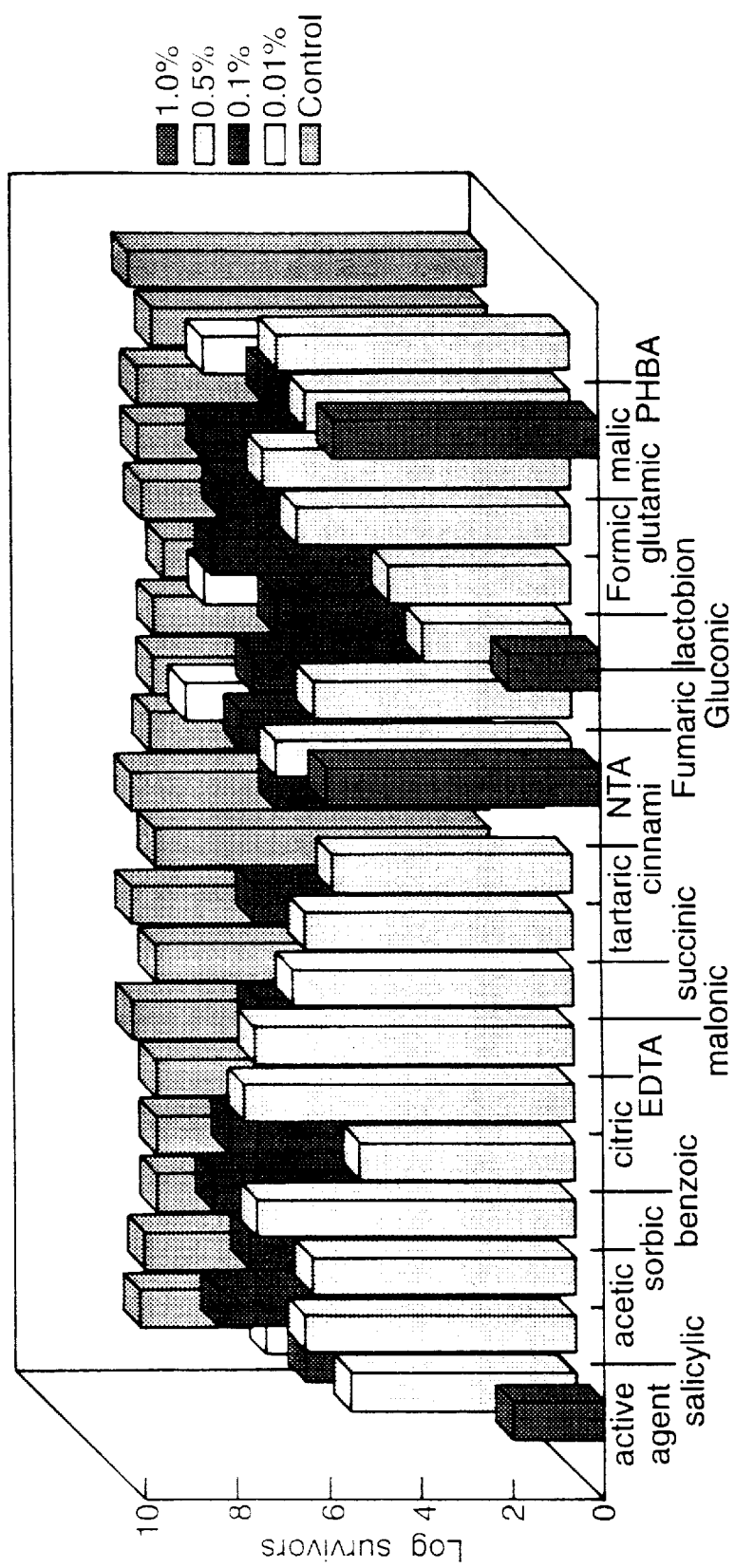

FIGS. 12*a*, *b* and *c* show the results of the experiments 23–25 into the effect of different concentrations (0.01%–1.0%) of the (B):acid mixtures against the three micro-organisms.

EXPERIMENT 23

Effect on S.aureus, FIG. 12a.

EXPERIMENT 24

Figure 12B:
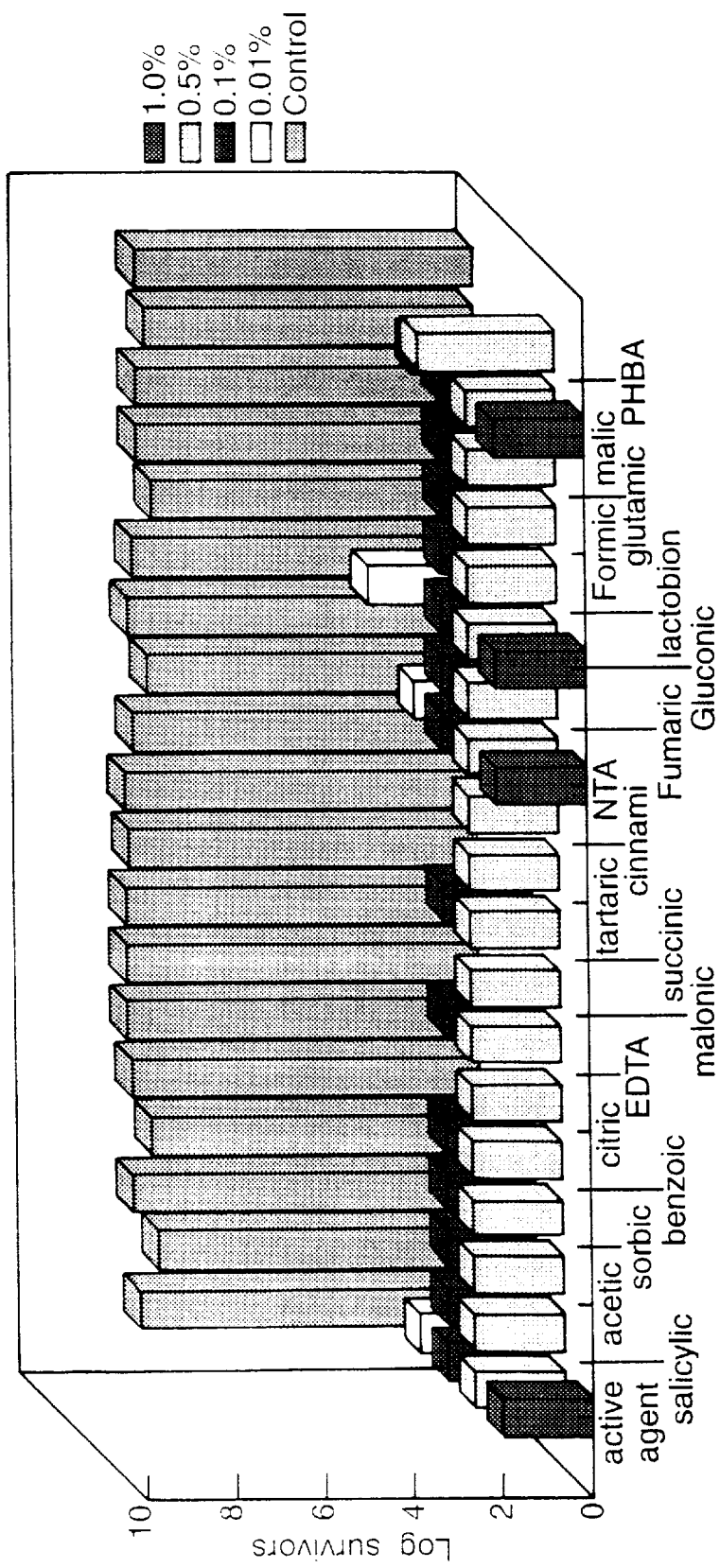

Effect on P.aeruginosa, FIG. 12b.

EXPERIMENT 25

Figure 12C:
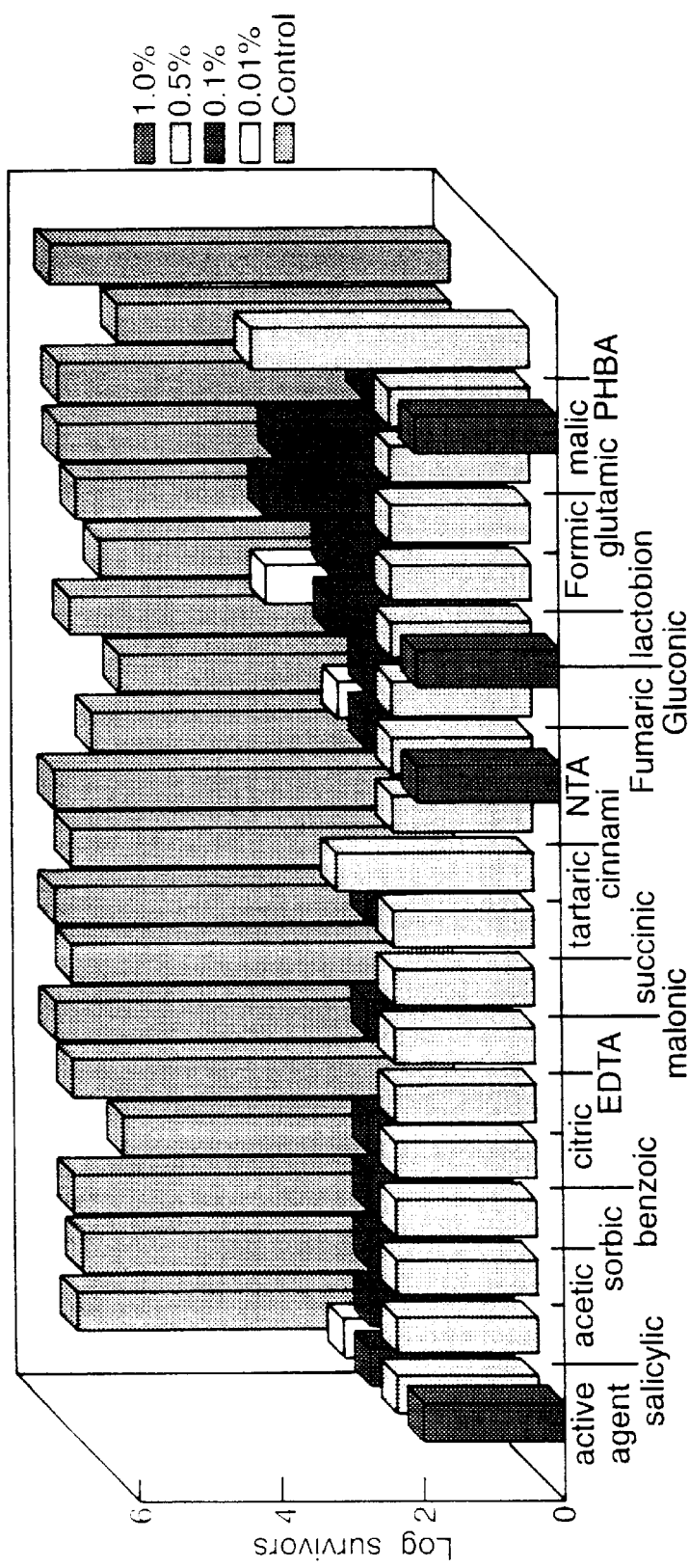

Effect on S.cerevisiae, FIG. 12c.

Investigation Into the Biocidal Effect of Different (H):acid Mixture Concentrations on the Microorganisms, (Experiments 26–28)

Figure 13A:
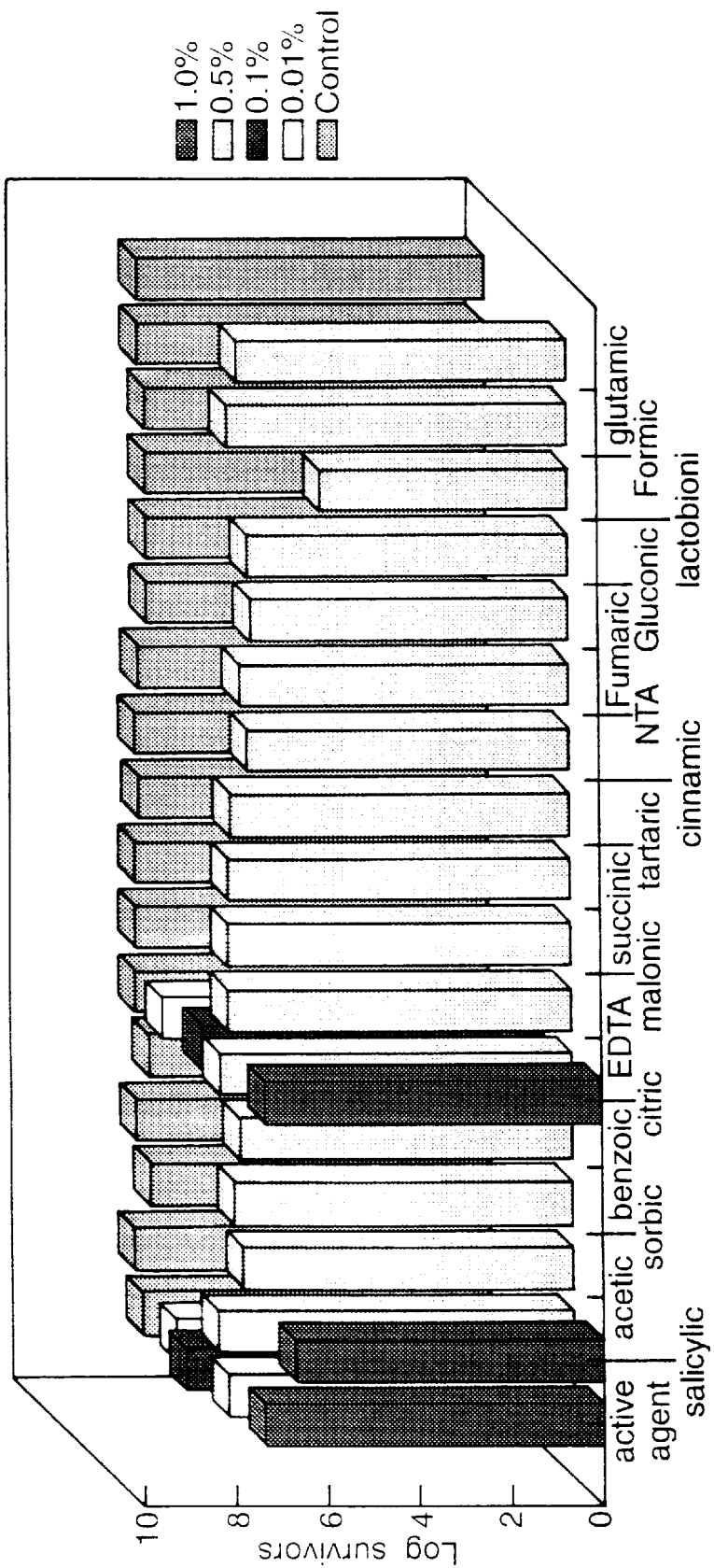

FIGS. 13a, b and c show the results of the experiments 26–28 into the effect of different concentrations (0.01%–1.0%) of the (H):acid mixtures against the three micro-organisms.

EXPERIMENT 26

Effect on S.aureus, FIG. 13a.

EXPERIMENT 27

Figure 13B:
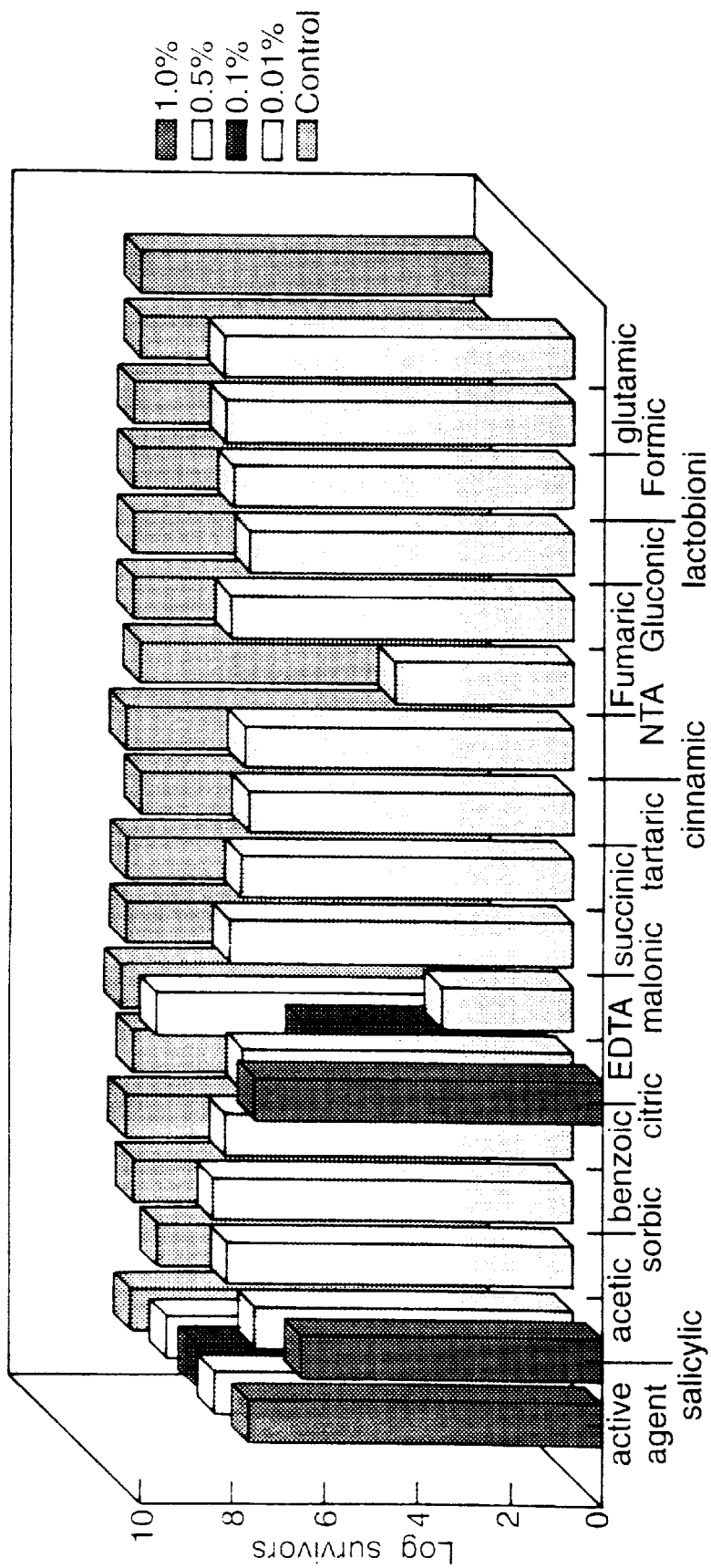

Effect on P.aeruginosa, FIG. 13b.

EXPERIMENT 28

Figure 13C:
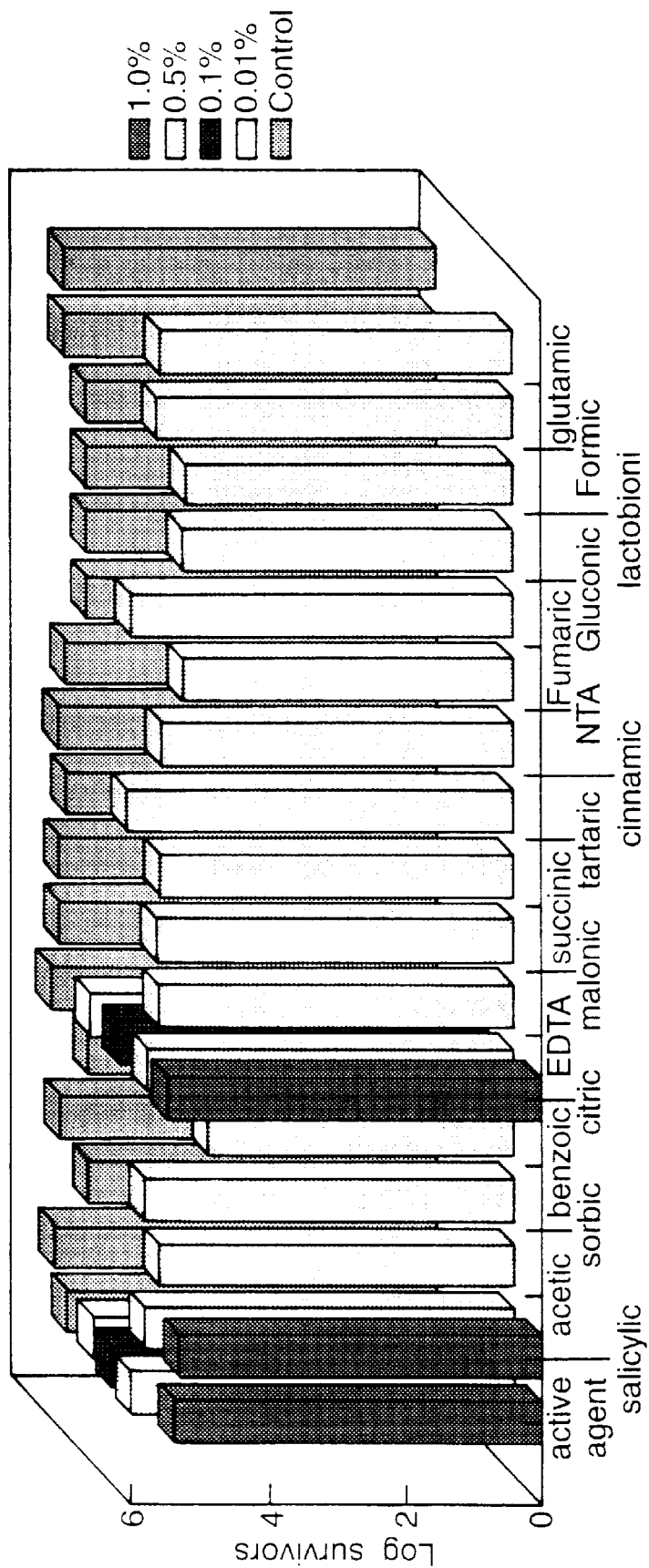

Effect on S.cerevisiae, FIG. 13c.

Investigation Into the Synergistic Factor in the Active Agent:Acid Mixtures

The following equation was used to find the synergistic factor:

Log reduction$_{total}$=log reduction$_{acid}$+log reduction$_{active\ agent}$+$\sigma_{SF}$ where $\sigma_{SF}$ (the Synergistic Factor) is positive if synergistic, negative if antagonistic.

Delineating the effect of the acid and the active agent from the effect of the mixtures was important in establishing whether a synergistic effect was present or not.

The total log reduction can be described by the following equation:

log reduction$_{obs}$=log reduction$_{active\ agent}$+log reduction$_{acid}$+$\sigma_{SF}$ Where:

log reduction$_{obs}$=total log reduction in organisms observed, log reduction$_{active\ agent}$=log reduction in organisms due to the effect of the surfactant alone, log reduction$_{acid}$=log reduction in organisms due to the acid alone, $\sigma_{SF}$, the synergistic factor, is the added log reduction observed due to the combination of both the acid and surfactant. This factor can be positive (synergistic) or negative (antagonistic).

The biocidal activity of the active agent is influenced by such factors as temperature, concentration, pH, chain length, permeability and head group charge. The biocidal activity of the acid is influenced by, for example, time of contact, permeability, pK$_a$, pH and concentration. Thus the Synergistic Factor is also influenced by these things since it is dependent on both. Tables 8, 9 and 10 show the $\sigma_{SF}$ factors calculated for the various active agent:acid mixtures at a concentration of 0.5% (acid and surfactant) at pH=5 at room temperature. One difficulty encountered in calculating these factors was, when the sum of the individual active agent and acid contributions are greater than the control number of organisms less the lowest recorded survival number (normally log 2) i.e. if the control number of organisms was log 7.2, and the log reduction$_{active\ agent}$=5.5 and the log reduction$_{acid}$=1.8, then the actual $\sigma_{SF}$ could not be calculated if it acted synergistically and a maximum value could only be given if it was antagonistic.

TABLE 8

Synergistic factors for active agent/weak acid mixtures;
S. aureus, pH = 5, 0.5% actives

| | A | D | C | F | B | H | E | G |
|---|---|---|---|---|---|---|---|---|
| salicylic | −1.45 | 0.3 | <−3.92 | 0.15 | −0.91 | 0.45 | 0.07 | −0.08 |
| acetic | <−2.2 | 0.54 | ud | −0.46 | −1.27 | 0.08 | −0.36 | 0.08 |
| sorbic | ud | 0.2 | <−3.58 | 0.73 | −2.33 | 0.28 | 0.22 | −0.64 |
| benzoic | ud | −0.7 | <−4.63 | −0.43 | −1.12 | −0.89 | −0.9 | −1.04 |
| citric | ud | 0.26 | −3.69 | 0.1 | −2.14 | −0.01 | 0.45 | −0.48 |
| EDTA | ud | 0.53 | <−3.27 | 0.93 | −2.54 | 0 | −0.38 | −0.25 |
| malonic | ud | | | −0.89 | −1.67 | −0.44 | | |
| tartaric | ud | | | −0.25 | −0.16 | 0.25 | | |
| NTA | ud | | | 0.64 | −1.92 | 0.13 | | |
| fumaric | <−0.86 | | | −0.06 | −1.12 | 0.37 | | |
| gluconic | ud | | | 2.09 | 0.88 | 0.17 | | |
| lacto-bionic | ud | | | 0.45 | 0.8 | 1.92 | | |
| glutamic | ud | | | −0.44 | −2.58 | −0.46 | | |
| malic | ud | | | 0.27 | −1.24 | −0.01 | | |
| PHBA | <−2.3 | | | | −1.45 | | | | ud = undetermined; log reduction (active agent) + log reduction (acid) > total count − 2

TABLE 9

Synergistic factors for active agent/weak acid mixtures;
P. aeruginosa, pH = 5, 0.5% actives

| | A | D | C | F | B | H | E | G |
|---|---|---|---|---|---|---|---|---|
| salicylic | 1.65 | −0.68 | ud | 0.28 | ud | −0.28 | 3.11 | −0.51 |
| acetic | 0 | 0.71 | ud | 0.4 | >0.09 | 0.18 | 2.93 | −0.18 |
| sorbic | 1.76 | >1.88 | ud | 0.41 | ud | 0.18 | 2.44 | 0.31 |
| benzoic | 1.61 | −2.1 | ud | 0.04 | ud | −0.32 | 0.04 | −0.67 |
| citric | 3.95 | 1.57 | ud | 0.37 | >0.01 | 0.62 | 3.3 | −0.4 |
| EDTA | >2.65 | ud | ud | 2.1 | ud | 2.41 | >2.43 | −0.7 |
| malonic | −0.3 | | | 0.07 | ud | −0.02 | | |
| tartaric | 0.38 | | | 0.15 | ud | 0.6 | | |
| NTA | >5.81 | | | >5.39 | ud | 3.66 | | |
| fumaric | 0.15 | | | 0.02 | >0.01 | 0.19 | | |
| gluconic | 0.12 | | | 3.93 | ud | 0.49 | | |
| lactobionic | 0.32 | | | 2.45 | ud | 0.51 | | |
| glutamic | −0.48 | | | −2.73 | ud | −0.64 | | |
| malic | 1.46 | | | −0.06 | ud | 0.22 | | |
| PHBA | 0.13 | | | | <−1.18 | 0.19 | | | ud = undetermined; log reduction (active agent) + log reduction (acid) > total count − 2

TABLE 10

Synergistic factors for active agent/weak acid mixtures;
S. aureus, pH = 5, 0.5% actives

| | A | D | C | F | B | H | E | G |
|---|---|---|---|---|---|---|---|---|
| salicylic | −2.88 | −1.58 | ud | 1.45 | ud | 0.29 | 0.21 | 0.79 |
| acetic | −2.14 | ud | ud | −0.49 | ud | −0.18 | 0.33 | −0.02 |
| sorbic | −2.21 | ud | ud | 1.15 | ud | 0.02 | −0.09 | 0.17 |
| benzoic | −2.28 | ud | ud | 1.48 | ud | 0.79 | 0.6 | 0.52 |
| citric | −1.92 | ud | ud | 0.85 | ud | 0.1 | −0.06 | −1.75 |
| EDTA | <−1.08 | ud | ud | 1.22 | ud | 0.27 | 0.5 | 0.34 |
| malonic | −0.07 | | | 1.1 | ud | 0.36 | | |
| tartaric | <−1.43 | | | ud | <−0.52 | −0.26 | | |
| NTA | −0.23 | | | 1.89 | ud | 0.26 | | |
| fumaric | <−2.37 | | | 0.93 | ud | −0.55 | | |
| gluconic | <−1.77 | | | ud | ud | −0.85 | | |

TABLE 10-continued

Synergistic factors for active agent/weak acid mixtures;
S. aureus, pH = 5, 0.5% actives

|  | A | D | C | F | B | H | E | G |
|---|---|---|---|---|---|---|---|---|
| lactobionic | ud |  |  | 1.69 | ud | 0.3 |  |  |
| glutamic | −0.97 |  |  | 1.52 | ud | 0.26 |  |  |
| malic | 0.51 |  |  | 1.67 | ud | 0.52 |  |  |
| PHBA | −2.94 |  |  |  | <−1.72 | 0.1 |  |  | ud = undetermined; log reduction (active agent) + log reduction (acid) > total count − 2

Conclusions from table 8:

$\sigma_{SF}$ factors for S.aureus, (gram positive bacteria).

The values, table-8, show the effects of the various acids used in combination with the active agents.

(B) gave negative sigma factors especially with polyacids such as sorbic, citric and EDTA.

With (A) where a sigma factor could be obtained, a strong antagonistic effect was observed, e.g. salicylate=−1.45.

Conclusions from table 9:

$\sigma_{SF}$ factors for P.aeruginosa, (gram negative bacteria).

A difference to the gram positive bacteria was observed (table 9). The acid:(A) mixtures showed strong synergies, especially with the chelating acids—NTA gives a synergistic factor of over 5.8 log units.

Conclusions from table 10:

$\sigma_{SF}$ factors for S.cervisiae

With (A) the sigma factors were large and negative, as found in some cases with S.aureus.

Comment on these conclusions from tables 8, 9 and 10:
The inventors postulate that some of the reasons for the variations of the $\sigma_{SF}$ factors with the different active agents may be due to reaction of the active agent with the acid and/or reaction of the acid and/or active agent with the outer walls of the bacteria inhibiting/aiding the effect of each other. The large negative effect of (B) with S.aureus is probably due to a reaction between the amine end of the surfactant and the techoic acids of the murein layer, this layer is smaller and less important in the gram negative bacteria. The large $\sigma_{SF}$ values for the chelating ligands may be due to them becoming more permeable, crossing the membrane more easily, and once inside, dissociating—like a weak acid—but then chelating metal ions such as calcium within the cell (NTA is smaller molecule and at the lower pH would be more permeable than EDTA). It is thought that this is a stronger effect than disruption of proton-motive force and therefore leads to the greater log reduction observed. At pH 7 EDTA has a stronger effect than NTA as a preservative, which suggests that at the higher pH strength of calcium complexation is the more prominent effect rather than permeability.

Following the Above Results, Further Research Was Carried out to Optimize the Composition of the Cleaners/Disinfectants According to the Present Invention.

A first composition according to the present invention was tested for its biocidal activity at a concentration of 1,0% w/w.

Composition:

| Formulation 1 (disinfectant) % as supplied as 100% Raw material: | | |
|---|---|---|
| (2) sodium hydroxide (50%) | 10.00 | 5.00 |
| (3) 1.3 propanediamine-n-3- | 5.50 | 1.65 |
| aminopropyl (30%) | | |
| (4) alkyl (C9-15) dimethylamine betaine (30%) | 5.00 | 1.50 |
| (5) citric acid anh | 8.40 | 8.40 |
| (6) sodium carbonate (light) | 1.00 | 1.00 |
| (7) sodium tetra borate 10 h2o | 1.00 | 1.00 |
| (1) water (demineralized) up to | 100.00 | 100.00 |

To yield formulation 1, the raw materials were mixed in the order given in brackets.

Specification of formulation 1:

Appearance: clear not viscous colourless liquid

Relative density (20° C.)

Viscosity: 1.085 pH (1% solution): 9.5–10.0 (demi water)

The efficacy of the composition (formulation 1) was evaluated in a test solution representing clean conditions. The test was performed according to the Quantitative European Suspension Test (E.S.T) method, as described under 3), above for assessing bactericidal and fungicidal activity, as follows:

Suspensions of the microorganisms were added to a solution containing formulation 1. After a period of exposure (5 minutes) at a temperature (20° C.), the fraction of surviving organisms was determined. One variant was tested:

a. with 0.03% bovine serum albumin (B.S.A.)in the test solution representing clean conditions.

Test organisms

The effect was assessed on both Gram negative and Gram positive bacteria and a yeast. The test strains used were:

proteus mirabilis ATCC 14153;

pseudomonas aeruginosa ATCC 15442;

saccharomyces cerevisiae ATCC 9763;

staphylococcus aureus ATCC 6538;

streptococcus faecium DVG 8582.

Calculation of the microbiocidal effect:

The microbicidal effect due to the action of the disinfectant in 5 minutes at 20° C. ($ME^{20}_5$) is expressed by the formula:

$$ME^{20}_5 = \log(N_c) - \log(N_D),$$

Where, $N_c$ is the number of colony forming units per ml of the test mixture without disinfectant, $N_D$ is the number of colony forming units per ml of the test mixture after the action of the disinfectant.

It is generally preferable that a disinfectant preparation in the lowest use dilution induces a microbicidal effect ($ME^{20}_5$) of at least 5 logarithmic reductions for each of the test organisms.

The results of the investigation, carried out at a pH of 9, are summarized in table 11, below.

Tested under clean conditions all the test organisms showed a reduction of at least 5 logarithmic cycli after 5 minutes exposure to the test composition at a concentration of 1.0% w/w.

Table 11 Microbicidal effect ($ME^{20}_5$) of formulation 1:

test concentration: 1.0% W/W bovine serum albumine: 0.03% time: 5 minutes
temperature: 20° C.

| Test organism | log $N_C$ (cfu*/ml) | log $N_D$ (cfu/ml) | $ME^{20}{}_5$ |
|---|---|---|---|
| Proteus mirabilis ATCC 14153 | 6.7 | <1 | >5.7 |
| Pseudomonas aeruginosa ATCC 15442 | 6.6 | <1 | >5.6 |
| Saccharomyces cerevisiae ATCC 9763 | 6.1 | <1 | >5.1 |
| Staphylococcus aureus ATCC 6538 | 7.0 | <1 | >6.0 |
| Streptococcus faecium DVG 8582 | 6.5 | <1 | >5.5 | cfu: colony forming units

Three further suspension tests were carried out to further determine the biocidal activity of formulation 1, on one or more of the following microorganisms.

| Key | microorganism | id number |
|---|---|---|
| Sa | Staphylococcus aureus | ATCC 6538 |
| Sc | Saccharomyces cerevisiae | ATCC 9763 |
| Ps | Pseudomonas aeruginosa | ATCC 15442 |
| Ef | Enterococcus faecium | DVG 8582 |
| Pm | Proteus mirabilis | ATCC 14153 |
| List | Listeria monocytogenes | Type 4 b |
| Sal | Salmonella choleraesuis | ATCC 13311 (previously S.typhimurium) |

Suspension test 1

Conditions

| | |
|---|---|
| Temperature | 20 ± 1° C. |
| Contact time | 5 min ± 5 sec |
| Soiling | 0.03% BSA |
| Water | 17° Gh |
| Inactivation | standard in buffer + horse serum |
| Concentration | 1.0% |

Results of suspension test 1

| MICROORGANISM | Sa LDR | Ef LDR | Ps LDR | Sc LDR | Pm LDR |
|---|---|---|---|---|---|
| Blanks in log | 8.5 | 7.5 | 8.9 | 7.0 | 9.0 |
| Formulation 1 | >7.5 | >6.5 | >7.9 | >6.0 | >8.0 |

LDR = Log reduction

Suspension test 2

Conditions

| | |
|---|---|
| Temperature | 20 ± 1° C. |
| Contact time | 5 min ± 5 sec |
| Soiling | 0.03% BSA |
| Water | 17° Gh |
| Inactivation | standard in buffer + horse serum |
| Concentration | 0.5% |

Results of suspension test 2

| MICROORGANISMS | Sa LDR | Ef LDR | Ps LDR | Sc LDR | Pm LDR | Sal LDR | List LDR |
|---|---|---|---|---|---|---|---|
| Blanks in log | 8.9 | 7.4 | 8.9 | 7.5 | 9.0 | 9.1 | 8.0 |
| Formulation 1 | >7.8 | >6.9 | 6.0 | >6.0 | >8.1 | >8.0 | >7.9 |

LDR = Log reduction

Suspension test 3

Conditions

| | |
|---|---|
| Temperature | 20 ± 1° C. |
| Contact time | 5 min ± 5 sec |
| Soiling | 0.03% BSA |
| Water | 17° Gh |
| Inactivation | standard in buffer + horse serum |
| Concentration | 0.5%, 0.4%, 0.3% |

Results of suspension test 3

| MICROORGANISM | Sa LDR | Ef LDR | Ps LDR | Sc LDR | Pm LDR | Sal LDR | List LDR |
|---|---|---|---|---|---|---|---|
| Blanks in log | 8.9 | 7.4 | 8.9 | 7.5 | 9.0 | 9.1 | 8.0 |
| Formulation 1 0.5% | >7.8 | >6.9 | 6.0 | >6.0 | >8.1 | >8.0 | >7.9 |
| Formulation 1 0.4% | >7.8 | >6.9 | >3.6 | >6.0 | 5.4 | >8.0 | >7.9 |
| Formulation 1 0.3% | >7.8 | >6.9 | 1.9 | >6.0 | 3.1 | >8.0 | >7.9 |

LDR = Log reduction

A second formulation of the composition according to the present invention was also subjected to two suspension tests. Formulation 2 (detergent % as supplied as sanitizer) 100%

| Raw material: | | |
|---|---|---|
| (2) sodium hydroxide (50%) | 10.00 | 5.00 |
| (3) 1.3 propanediamine-n-3-aminopropyl (30%) | 6.50 | 1.95 |
| (4) alkyl (C9-15) dimethylamine betaine (30%) | 5.00 | 1.50 |
| (5) citric acid anh | 8.40 | 8.40 |
| (6) fatty acid alcohol (C9-11) ethoxylate 5 EO | 4.00 | 4.00 |
| (7) sodium carbonate (light) | 1.00 | 1.00 |
| (8) sodium tetra borate 10 h2o | 1.00 | 1.00 |
| (1) water (demineralized) up to | 100.00 | 100.00 |

Production method:

The raw materials were mixed in the in order given in brackets.

Specification of formulation 2:

Appearance: clear non viscous colourless liquid

Relative density (20° C.): 1.086 pH (1% solution): 9.5–10.0 (demi water)

Suspension test 1 to determine the mocrobiocidal efficiency of formulation 2.

| Conditions | |
|---|---|
| Temperature | 20 ± 1° C. |
| Contact time | 5 min ± 5 sec |
| Soiling | 1% BSA |
| Water | 17° Gh |
| Inactivation | standard in buffer + horse serum |
| Concentration | 0.5%, 1% |

Results of suspension test 1

| MICROORGANISM | Sa LDR | Ef LDR | Ps LDR | Sc LDR | Pm LDR | Sal LDR | List LDR |
|---|---|---|---|---|---|---|---|
| Blanks in log | 8.9 | 7.4 | 8.9 | 7.5 | 9.0 | 9.1 | 8.0 |
| Formulation 2, 1% BSA, 0.5% conc. | >5.4 | >1.7 | 1.9 | >0.5 | >9.0 | >3.6 | >7.0 |
| Formulation 2, 1% BSA, 1% conc. | >7.7 | >6.7 | 7.8 | 5.6 | 7.3 | | |

LDR = Log reduction

| Suspension test 2 Conditions | |
|---|---|
| Temperature | 20 ± 1° C. |
| Contact time | 5 min ± 5 sec |
| Soiling | 1% BSA |
| Water | 17° Gh |
| Inactivation | standard in buffer + horse serum |
| Concentration | 0.5%, 0.4%, 0.3% |

Results of suspension test 3

| MICROORGANISM | Sa LDR | Ef LDR | Ps LDR | Sc LDR | Pm LDR | Sal LDR | List LDR |
|---|---|---|---|---|---|---|---|
| Blanks in log | 8.9 | 7.9 | 9.1 | 7.0 | >8.19.0 | 9.0 | 8.9 |
| Formulation 2 0.5% | >7.8 | >6.9 | 5.1 | >6.0 | >8.1 | >8.0 | >7.9 |
| Formulation 2 0.4% | >7.8 | >6.9 | 4.8 | >6.0 | 5.4 | >8.0 | >7.9 |
| Formulation 2 0.3% | >7.8 | >6.9 | 2.0 | >6.0 | 3.1 | >8.0 | >7.9 |

LDR = Log reduction

REFERENCE

1. Jones, M. V., Food Preservative Interactions, PCW 851201

We claim:

1. A disinfecting composition comprising a solubilizing agent comprising water, and an alkyl amine of formula:

$$R_1NH(CH_2)_3NH(CH_2)_3NH_2,$$

wherein $R_1$ is $C_{12}$ alkyl, and an alkyl betaine, wherein the ratio of the alkyl amine to alkyl betaine is in the range of from 1:3 to 3:1.

2. The composition according to claim 1, further comprising a cleaning agent.

3. The composition according to the claim 1, wherein the alkyl betaine has the general formula:

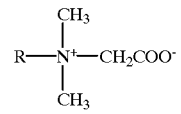

wherein R is $C_9$–$C_{15}$ alkyl.

4. The composition according to claim 1 comprising 1–15 wt. % of the alkylamine and the alkyl betaine.

5. The composition according to claim 2, wherein the cleaning agent is a fatty alcohol ethoxylate.

6. The composition according to claim 1 wherein the ratio of alkyl amine to alkyl betaine is 1:1.

7. The composition according to claim 1, further comprising an organic acid.

8. The composition according to claim 7, wherein the organic acid is selected from the group consisting of salicylic acid, acetic acid, sorbic acid, benzoic acid, lactic acid, citric acid, malonic acid, tartaric acid, gluconic acid, lactobionic acid, formic acid, malic acid, parabenzoic acid, and peracetic acid.

9. The composition according to claim 1, further comprising a buffer.

* * * * *